US 6,692,432 B1

(12) United States Patent
Yarush et al.

(10) Patent No.: US 6,692,432 B1
(45) Date of Patent: Feb. 17, 2004

(54) HAND-HELD PORTABLE CAMERA FOR PRODUCING VIDEO IMAGES OF AN OBJECT

(75) Inventors: Don Yarush, Henderson, NV (US); Todd Devos, Las Vegas, NV (US); Gary Handelin, Carson City, NV (US); Martin G. Sosa, Carson City, NV (US)

(73) Assignee: East Giant Limited (HK)

( * ) Notice: Subject to any disclaimer, the term of this patent is extended or adjusted under 35 U.S.C. 154(b) by 214 days.

(21) Appl. No.: 09/690,095

(22) Filed: Oct. 16, 2000

Related U.S. Application Data

(63) Continuation of application No. 08/828,147, filed on Mar. 24, 1997, which is a continuation-in-part of application No. 08/680,174, filed on Jul. 15, 1996, now Pat. No. 5,879,289.

(51) Int. Cl.⁷ .............................. A61B 1/04; A61B 1/07
(52) U.S. Cl. ....................... 600/179; 600/109; 600/127; 600/130; 600/131; 600/167; 600/182
(58) Field of Search ................................. 600/112, 110, 600/109, 179, 127, 130, 131, 167, 182, 160, 178, 452, 558; 348/65, 68, 66, 70, 71, 77, 79, 80; 433/29, 30

(56) References Cited

U.S. PATENT DOCUMENTS

| | | | |
|---|---|---|---|
| 3,581,140 A | 5/1971 | Paquette | 313/110 |
| 3,582,637 A | 6/1971 | Cecil | 240/1 EL |
| 3,597,647 A | 8/1971 | Rishton | 313/110 |
| 3,638,643 A | 2/1972 | Hotchkiss | 128/9 |
| 3,681,592 A | 8/1972 | Hugelshofer | 240/47 |
| 3,721,815 A | 3/1973 | Wall | 240/10 R |
| 3,770,338 A | 11/1973 | Helmuth | 350/96 R |
| 4,241,382 A | 12/1980 | Daniel | 362/32 |
| 4,413,278 A | 11/1983 | Feinbloom | 358/93 |
| 4,580,198 A | 4/1986 | Zinnanti, Jr. | 362/203 |
| 4,601,284 A | 7/1986 | Arakawa et al. | 128/6 |
| 4,602,281 A | 7/1986 | Nagasaki et al. | 358/98 |
| 4,633,304 A | 12/1986 | Nagasaki | 358/98 |
| 4,651,202 A | 3/1987 | Arakawa | 358/98 |
| 4,685,452 A | 8/1987 | Riester | 128/9 |
| 4,727,859 A | 3/1988 | Lia | 128/6 |

(List continued on next page.)

FOREIGN PATENT DOCUMENTS

| | | | | |
|---|---|---|---|---|
| AU | 891888 | 12/1993 | | |
| DE | G 94 05 345.6 | 9/1994 | | A61B/1/04 |
| EP | 0 573 158 A1 | 12/1993 | | A61B/1/00 |
| FR | 2 695 785 | 9/1962 | | 5/28 |
| FR | 2 695 785 | 9/1992 | | 5/28 |
| GB | 273473 | 7/1927 | | |
| WO | WO 93/15648 | 8/1993 | | 128/6 |
| WO | WO 97/15144 | 4/1997 | | H04N/7/18 |

OTHER PUBLICATIONS

Cudda® Products Corp. Distributor Price Information Brochure, Sep. 1995.
EarCrafters, Inc. Introduces the Most "User Friendly" Portable S–Video Otoscope on the Market, *The Hearing Journal*, vol. 47, No. 12, Dec. 1994.

(List continued on next page.)

*Primary Examiner*—John P. Leubecker
(74) *Attorney, Agent, or Firm*—Workman Nydegger; David B. Dellenbach

(57) ABSTRACT

A portable, hand-held endoscopic camera having all of the necessary components for performing endoscopic procedures comprises power source means, lens means, light source means, and video camera means. The portable endoscopic camera is adaptable to a wide variety of systems and includes a low wattage light source means. The camera is self-contained. A kit is also provided, the kit having all of the components necessary for performing endoscopic procedures.

15 Claims, 20 Drawing Sheets

U.S. PATENT DOCUMENTS

| | | | | |
|---|---|---|---|---|
| 4,736,734 A | | 4/1988 | Matsuura et al. .............. | 128/6 |
| 4,742,819 A | | 5/1988 | George | |
| 4,756,304 A | | 7/1988 | Watanabe ...................... | 128/6 |
| 4,807,594 A | | 2/1989 | Chatenever .................... | 128/4 |
| 4,823,244 A | * | 4/1989 | Alaybayoglu et al. | |
| 4,844,071 A | | 7/1989 | Chen et al. ..................... | 128/6 |
| 4,851,866 A | | 7/1989 | Ciarlei et al. ................. | 354/62 |
| 4,858,001 A | | 8/1989 | Milbank et al. .............. | 358/98 |
| 4,883,061 A | | 11/1989 | Zeimer ...................... | 128/665 |
| 4,895,138 A | | 1/1990 | Yabe ............................ | 128/6 |
| 4,905,670 A | | 3/1990 | Adair ......................... | 128/18 |
| 4,941,456 A | * | 7/1990 | Wood et al. .................. | 348/69 |
| 4,979,498 A | | 12/1990 | Oneda et al. ............... | 128/203 |
| 5,010,876 A | | 4/1991 | Henley et al. ................. | 128/6 |
| 5,042,915 A | | 8/1991 | Akutsu et al. .............. | 359/230 |
| 5,053,929 A | | 10/1991 | Le Gars ...................... | 362/32 |
| 5,083,059 A | | 1/1992 | Graham et al. ............. | 313/631 |
| 5,086,378 A | | 2/1992 | Prince ........................ | 362/103 |
| 5,117,154 A | | 5/1992 | Thomas et al. ............. | 313/634 |
| 5,125,394 A | | 6/1992 | Chatenever et al. ........... | 128/4 |
| 5,138,228 A | | 8/1992 | Thomas et al. ............. | 313/634 |
| 5,144,201 A | | 9/1992 | Graham et al. ............. | 313/634 |
| 5,205,280 A | | 4/1993 | Dennison, Jr. et al. ......... | 128/3 |
| 5,229,841 A | | 7/1993 | Taranowski et al. ........ | 356/406 |
| 5,241,170 A | | 8/1993 | Field, Jr. et al. ...... | 250/214 VT |
| 5,311,859 A | | 5/1994 | Monroe et al. ................. | 126/6 |
| 5,314,070 A | | 5/1994 | Ciarlei ........................ | 206/570 |
| 5,363,838 A | | 11/1994 | George ........................... | 128/6 |
| 5,363,839 A | | 11/1994 | Lankford ....................... | 128/9 |
| 5,408,268 A | * | 4/1995 | Shipp ......................... | 348/269 |
| 5,412,749 A | | 5/1995 | Sayegh et al. .............. | 385/115 |
| 5,487,661 A | * | 1/1996 | Peithman | |
| 5,498,230 A | | 3/1996 | Adair ......................... | 600/112 |
| 5,523,786 A | | 6/1996 | Parulski ...................... | 348/269 |
| 5,527,261 A | | 6/1996 | Monroe et al. ............. | 600/178 |
| 5,575,757 A | | 11/1996 | Kennedy et al. ............ | 600/167 |
| 5,591,119 A | | 1/1997 | Adair ......................... | 600/112 |
| 5,604,531 A | * | 2/1997 | Iddan et al. | |
| 5,717,806 A | * | 2/1998 | Pileski et al. | |
| 5,735,794 A | | 4/1998 | Koeda et al. ............... | 600/178 |
| 5,745,165 A | * | 4/1998 | Atsuta et al. .................. | 348/65 |
| 5,819,736 A | * | 10/1998 | Avny et al. .................. | 600/407 |
| 5,908,294 A | | 6/1999 | Schick et al. ................. | 433/29 |
| 5,983,039 A | * | 11/1999 | Aoki | |
| 5,984,860 A | | 11/1999 | Shan .......................... | 600/116 |
| 5,984,861 A | | 11/1999 | Crowley ..................... | 600/175 |
| 6,001,058 A | | 12/1999 | Sano et al. .................. | 600/132 |
| 6,004,263 A | | 12/1999 | Nakaichi et al. ............ | 600/176 |
| 6,007,485 A | | 12/1999 | Koeda et al. ............... | 600/178 |
| 6,080,101 A | | 6/2000 | Tatsuno et al. ............. | 600/112 |
| 6,124,883 A | | 9/2000 | Suzuki et al. .................. | 348/68 |
| 6,152,588 A | | 11/2000 | Scifres ....................... | 362/496 |
| 6,155,973 A | | 12/2000 | Howes et al. ............... | 600/112 |
| 6,193,401 B1 | | 2/2001 | Girkin et al. ............... | 362/551 |
| 6,196,691 B1 | | 3/2001 | Ochiai ......................... | 362/31 |

OTHER PUBLICATIONS

Cudda® Products Corp. Distributor Price Information Brochure, Sep. 1995.

EarCrafters, Inc. Introduces the Most "User Friendly" Portable S–Video Otoscope on the MArket, *The Hearing Journal*, vol. 47, No. 12, Dec. 1994.

Edmund Scientific Industrial Optics Division, Optics and Optical Instruments Catalog, pp. 1, 2, 230, and 2B1, Copyright 1998.

Product brochure for Machida, Inc.; *High Quality Fiberoptic Borescopes, Video Systems and Accessories for Non–Destructive Inspections*, Available upon information and belief at least as early as Mar., 2001.

Product brochure for Machida, Inc., *Machida 8mm Flexible Borescope Series, FBA–8 Series*, Available upon information and belief at least as early as Apr., 1992.

Product brochure for Machida, Inc., *Power Blending Borescope Kit, MA–KPDA2 System*, Available upon information and belief at least as early as Apr., 1998.

Product brochure for Machida, Inc., *Machida 3mm Flexible Borescope Series, FBA–3 Series*, Available upon information and belief at least as early as Apr., 1998.

Product brochure for Machida, Inc., *MAchida 4mm Flexible Borescope Series, FBA–4 Series*, Available upon information and belief at least as early as Apr., 1998.

Product brochure for Machida, Inc., *Machida 150 Watt Borescopic Light Source Model: RH–150A5*, Available upon information and belief at least as early as Mar., 2001.

Product brochure for Machida, Inc., *Lateral/Direct View Flexible Borescope, FBA–4–120T Designed for Pratt & Whitney Canada Engines Series PW100/PT6*, Available upon information and belief at least as early as Jun., 1994.

Product brochure for Machida, Inc., *Pratt & Whitney JT8D Combustion Chamber Inspection Kit Model MJ07200MA*, Available upon information and belief at least as early as Nov., 1994.

Product brochure for Machida, Inc., *6mm Flexible Borescope Series, FBA–6 Series*, Available upon information and belief at least as early as Apr., 1998.

Product brochure for Machida, Inc., *Machida High Intensity Borescope Light Source, RG–2500A*, Available upon information and belief at least as early as Mar., 2001.

Product brochure for Machida, Inc., *Small Diameter Modular Borescope System, MBS Series*, Available upon information and belief at least as early as Dec., 1994.

Product brochure for Machida, Inc.; *Blending Borescope System For Pratt & Whitney Engines*, Available upon information and belief at least as early as Mar., 2001.

Product brochure for Machida, Inc.; *Machida's Super High Resolution Borescopic Video System, MCV–8500 Series*, Available upon information and belief at least as early as Mar., 2001.

Product for Machida, Inc.; *Machida Fod Prevention Fiberscope Kit*, Available upon information and belief at least as early as Mar., 2001.

Product brochure for Machida, Inc.; *Machida Flexible Borescope, Model FBA–4–120T Lateral and Direct View*, Available upon information and belief at least as early as Mar., 2001.

Product brochure for Machida Inc.; *Machida Miniature Light Source AC/DC Model: RH–24N*, Available upon information and belief at least as early as Mar., 2001.

Product brochure for Machida, Inc.; *Introducing Machida's New, Affordable, Battery Operated Flexible Borescope, FBA–4B–100*, Available upon information and belief at least as early as Mar., 2001.

Product brichure for Machida, Inc.; *Machida Borescope Video Systems, Model MCV–510 & MCV–510S*, Available upon information and belief at least as early as Mar., 2001.

* cited by examiner

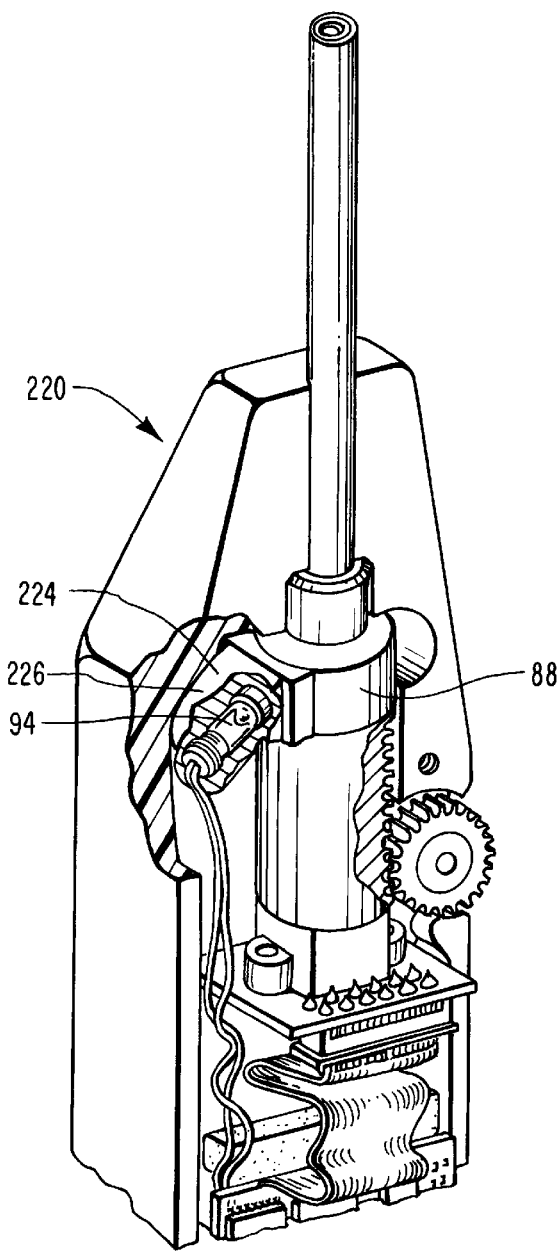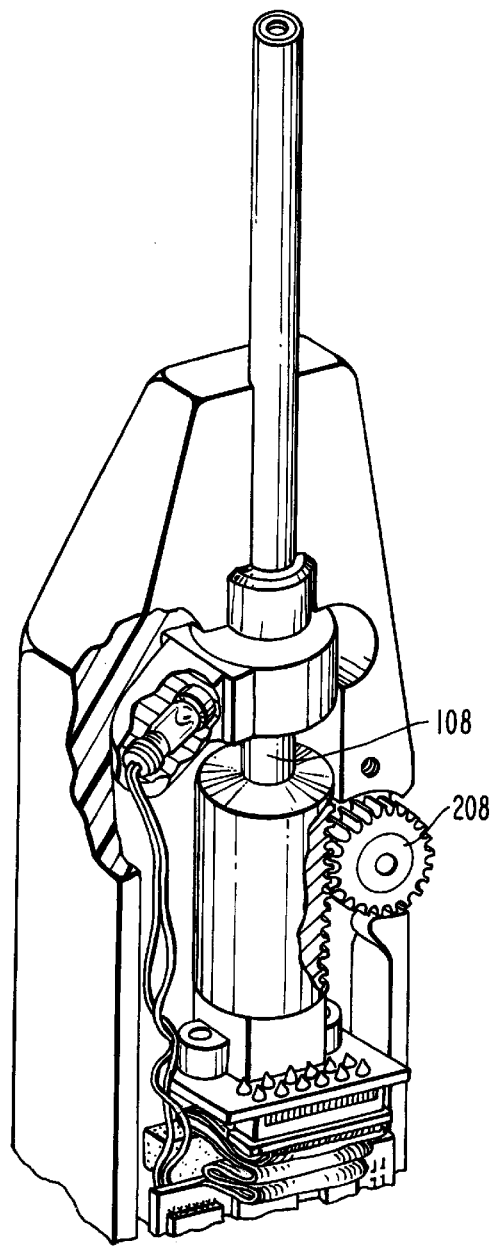
FIG. 10
FIG. 11

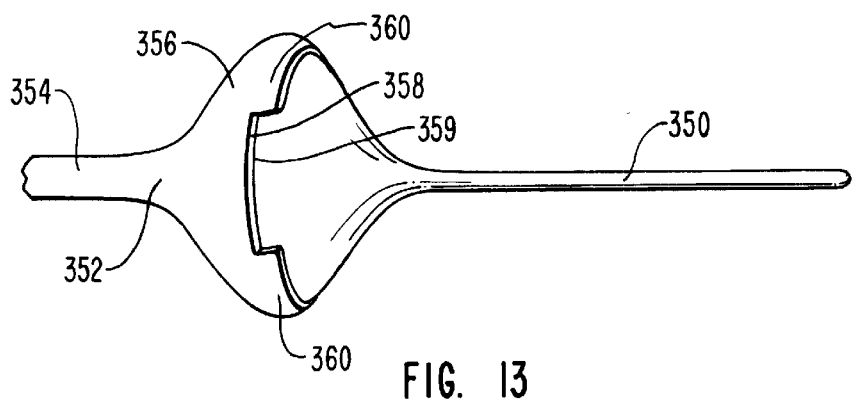
FIG. 13
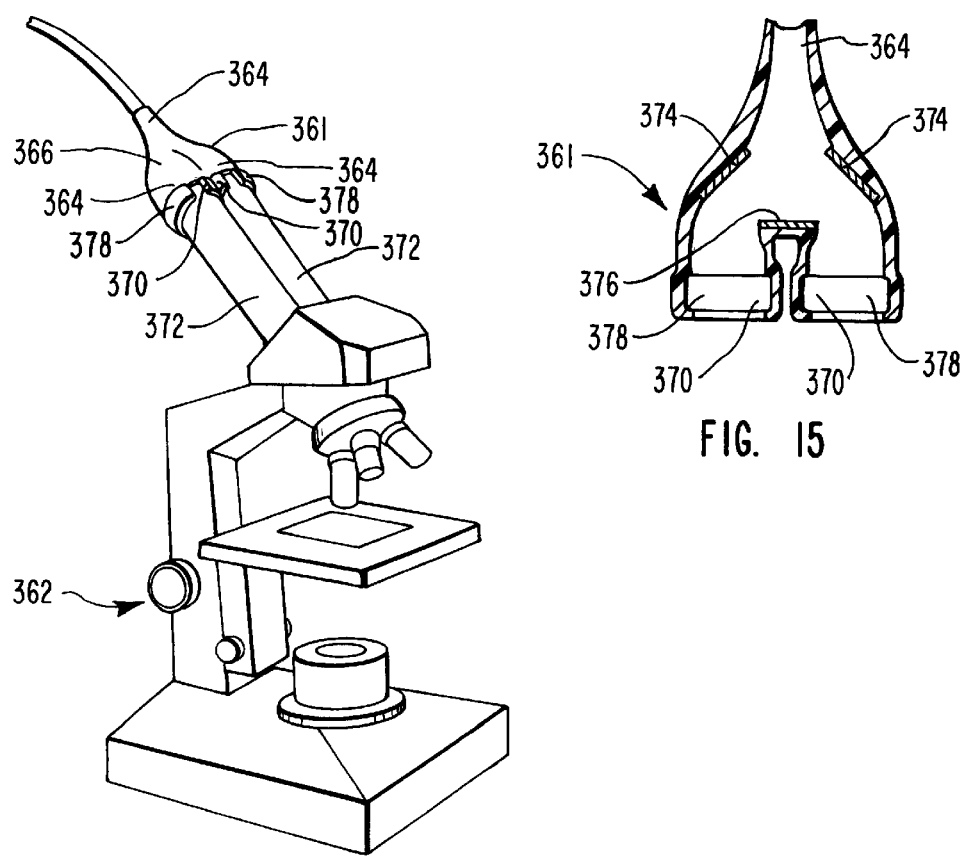
FIG. 14
FIG. 15

HAND-HELD PORTABLE CAMERA FOR PRODUCING VIDEO IMAGES OF AN OBJECT

This patent application is a continuation of a United States Patent Application entitled "Hand-Held, Portable Endoscopic Camera and Kit for Producing Video Images of an Object" filed Mar. 24, 1997, Ser. No. 08/828,147, to Yarush, et al, which is incorporated herein in its entirety by reference, and which is a continuation-in-part of a United States Patent Application entitled "Hand-Held, Portable Endoscopic Camera," filed on Jul. 15, 1996, application Ser. No. 08/680,174, to Yarush, et al, now U.S. Pat. No. 5,879,289, which is incorporated herein in its entirety by reference.

BACKGROUND OF THE INVENTION

1. The Field of the Invention

This invention relates to endoscopic cameras and more particularly, to a portable, hand-held endoscopic camera and a kit for producing video images of an object.

2. Related Applications

The field of endoscopy has greatly enhanced a practitioner's ability to penetrate objects to view internal mechanisms and other features with minimal intrusion. Endoscopes have broad reaching application in the field of diagnostic and therapeutic medicine, surgery, dentistry, computer inspection, customs inspection, plumbing, mining, automobile mechanics, veterinary medicine, aviation, remote control devices, safety equipment, monitoring devices, police investigations and in a variety of other settings in which detailed inspection is desired.

3. The Relevant Technology

A major challenge facing the field of endoscopy is the vast amount of equipment typically required. The equipment found in the prior art typically includes a large monitor, a light source, a power source and an endoscope. In addition, fiber optic and power cables are required to connect the monitor, light source, and power source to the endoscope. Typical such equipment is often permanently or semi-permanently installed in a tightly enclosed area, such as a dental office. Offices must typically be specially adapted to accommodate the cumbersome equipment, requiring expensive wiring of circuitry and the placement of plugs and cables within the room. Each individual room in a clinic is required to maintain the equipment and wiring if endoscopic capability is desired in the room.

Compounding the problem, the optic and power cables connecting the light source, power source and monitor to the endoscope are cumbersome to use. The cables must be dragged around the area to be viewed, wrapping them around the patient's body and objects within the room to look inside an ear or mouth, for example. Fiber optic cable is a rather stiff and inflexible glass cable which can be easily broken during such procedures. As the cables are flexed, the fiber optics may be broken. As the glass is broken, the image received is distorted and distortions known as "ghosts" appear on the monitor.

Generally, the longer the fiber optic cable employed in a particular procedure, the more light is needed. Typical light sources require high voltages, preventing use of battery operated systems. Thus, the power cables must typically be plugged into an electrical outlet mounted in the office.

The use of high intensity light sources also creates an inefficient use of space. The light source employed in many endoscopic systems is a large bulb, such as a halogen bulb, which generates a considerable amount of heat typically in the range of about 50 to 150 watts. When employed near a probe which is placed in a body cavity, the typical light source tends to heat the probe, which is uncomfortable or dangerous to sensitive body openings such as an ear. As a result, many light sources consist of a separate component having a large enclosure for housing the light source. A fan may be used to cool the light source or the connections thereto, creating an exhaust system, but also requiring additional energy and more space.

Other systems employ a heat sink to absorb the heat or a shield to buffer the heat, which also requires increased amounts of space. A heat sink is typically comprised of a conductive material, such as metal, which absorbs heat. The heat sink is typically located a certain distance away from the light bulb and the housing, drawing heat away from these areas which heat may adversely affect. Typically, a fan is then used to cool the heat sink.

An additional drawback to endoscopic technology typically found in the prior art is the requirement that the practitioner view a monitor which is located away from the patient or object under inspection. This often requires the physician to attempt to aim the endoscope at a precise, enclosed location while looking in a completely different direction, which is often difficult and cumbersome. In addition, typically if the practitioner desires to employ a different type of probe, the practitioner must often employ a different endoscope.

In addition, typical cord operated systems are not readily used in countries foreign to the United States. For example, typical endoscopic systems fail to readily convert to 220 volt, 50 cycle power sources which are commonly used in countries foreign to the United States, requiring the practitioner to employ a cumbersome transformer when travelling to countries foreign to the United States.

An additional drawback to typical high light intensity systems is the color distortion which often occurs when viewing a bodily orifice, for example. Because of the high intensity light employed, typical halogen systems often distort the color of bodily organs, such as the ear drum. Color distortion can result in a misdiagnosis of the condition of the organ.

SUMMARY AND OBJECTS OF THE INVENTION

It is, therefore, an object of the invention to provide a portable endoscopic camera.

Another object of the invention is to provide a portable, hand-held endoscopic camera that is self-contained, lightweight, and easy for a medical practitioner to manipulate.

It is a further object of the invention to provide a portable, hand-held endoscopic camera which features a lighting system capable of high-intensity illumination without creating an over abundance of heat.

It is a further object of the invention to provide a portable hand-held videoscopic camera having a low wattage light source means.

It is a further object of the invention to provide a hand-held, portable endoscopic camera which is operable in a cordless and a cord-operated mode.

It is a further object of the invention to provide a hand-held portable endoscopic camera having a variety of capabilities, including various video output capabilities, various power source capabilities, adjustable light sources, transmitting features, memory features, and adaptability to a variety of probes and adapters and a variety of existing endoscopic systems.

It is a further object of the invention to concentrate the light generated from a light source means into a desired location within the camera, allowing the practitioner to employ a low voltage light source, yet achieve high resolution of objects viewed by the camera.

It is a further object of the invention to provide improved resolution of objects viewed by the camera.

In response to this tremendous need in the art, the present invention provides a high resolution, hand-held, portable endoscopic camera which is selectively operable in a cordless and a cord-operated mode. The portable endoscopic camera of the present invention is compatible with a variety of output systems, light requirements, adapters, and probes, but does not rely on bulky fiber optic cables connecting the endoscope to the other equipment. The portable endoscopic camera features a light source which is capable of illuminating the endoscope, yet, at the same time is small enough that it does not rely on fans or heat sinks to prevent overheating. In one embodiment, the endoscopic camera contains all of the necessary equipment required to perform endoscopic procedures in a single, hand-held housing.

In one embodiment, the hand-held, portable endoscopic camera includes a lens system having dual roles. First, the lens system illuminates an object under examination through a fiber bundle that couples light from the light source means to the object. Second, the lens system translates an image of the illuminated object into video imaging circuitry which includes a charge coupled device ("CCD") array. A coupler optically couples the lens system to the video imaging circuitry. The video imaging circuitry converts the image of the object into video signals. The video imaging circuitry then outputs the video signals to a monitor. The practitioner then views the illuminated object on the video monitor.

In order to illuminate the object, in one embodiment, the lens system includes a fiber bundle that channels the light from the light source means to the object under examination. A power supply supplies electrical power both to the light source and to the video imaging circuitry. In one embodiment, a housing houses the lens system, video imaging circuitry, light source and power supply. This self-contained unit allows the practitioner to inspect a variety of objects without using cumbersome cords and cables. As will be discussed in detail, a variety of additional components are connected to or mounted integrally within the hand-held housing.

In one embodiment, a display monitor is integral with the hand-held, portable apparatus, allowing the practitioner to look in generally the same direction while orienting the camera and viewing the object under inspection. In another embodiment, the hand-held, portable endoscopic camera is capable of sending a signal to a monitor configured to receive signals as far as 300 feet away. Thus, rather than placing an endoscope in every room of a clinic, for example, a single unit can be used in a variety of rooms and can send transmissions to a centralized monitor for video capture, recording, and viewing.

The endoscopic camera is adapted to receive a variety of adapters and probes, depending upon the desired procedure. Since a change in procedure is often accompanied by a variation in light intensity, the disclosed camera is capable of delivering a variable light intensity for different types of fiber optic probes which may be employed.

If battery use and rechargeability is not desired on a certain occasion, it is possible to plug the hand-held, portable unit into an electrical outlet. In addition, it is possible to connect the hand-held, portable apparatus into a separate monitor, such as a wall or shelf mounted monitor. The hand-held unit is compatible with S-VHS and/or composite video output formats.

In order to accomplish the goal of providing good video resolution, yet avoiding the use of a heat sink or fan, a low wattage light bulb is employed. In order to use the light produced by the low wattage light bulb more efficiently, a sleeve is coupled to the lens means and light bulb and the light bulb is abutted against the lens means. One embodiment of the invention includes a kit for production of video images of an object.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which:

FIG. 10 is a partial view of yet another embodiment of a portable endoscopic camera with the lid of the housing removed.

FIG. 11 is a partial view of the portable endoscopic camera of FIG. 10 with the optical coupler adjusted in the proximal direction, exposing the proximal end of the lens tube.

FIG. 13 is a perspective view of a coupler for coupling the lens tube to a funnel-shaped probe.

FIG. 14 demonstrates a coupler used to adapt a portable endoscopic camera to a microscope.

FIG. 15 is a cross-sectional view of the coupler of FIG. 14.

DETAILED DESCRIPTION OF THE PREFERRED EMBODIMENTS

Figure 1:
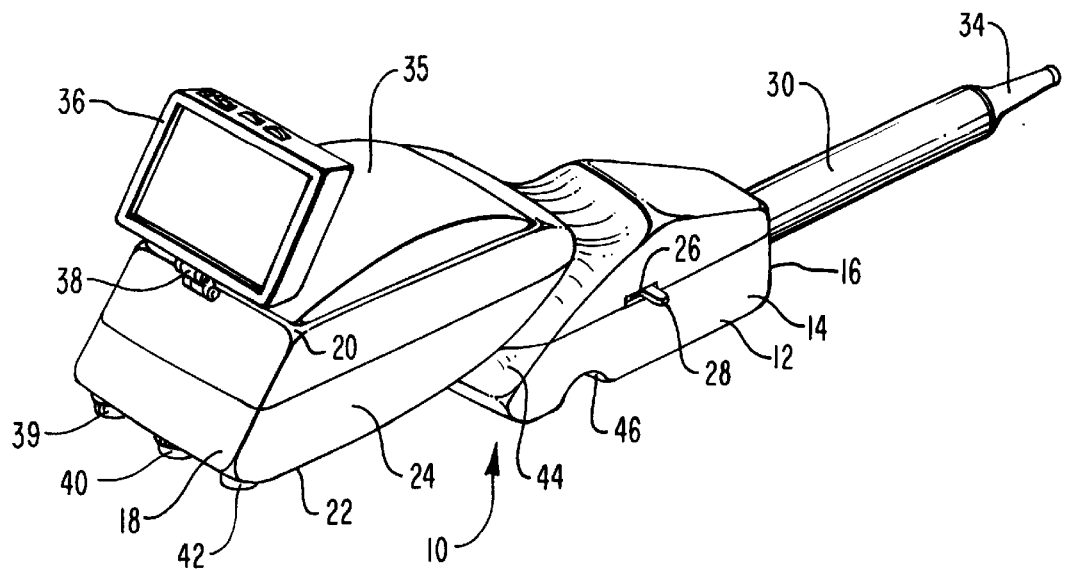
FIG. 1 is a perspective view of one embodiment of a portable endoscopic camera.

The headings contained in this application are for convenience of reference only and are neither intended, nor should they be construed, to be limiting in any respect.

A. Overview

The present invention relates to a portable, self-contained endoscopic camera. The camera is lightweight and is configured to rest comfortably in the hand of a medical professional or other user. In one embodiment, the camera contains all of the necessary components required to perform endoscopic procedures in a single, hand-held unit. The camera features: (i) an on-board, light source for illuminating the objects to be viewed with the endoscopic camera; (ii) video camera circuitry for converting optical images into video signals; and (iii) a lens system that translates images to the optical input of the video camera. As discussed in more detail below, the present invention converts optical images captured at the input end of the lens systems into video signals, which can then be recorded or viewed on either a video monitor that is integral to the hand-held unit or to an external video monitor or other output device. The present invention may also include an RF transmitter so that the resulting video signals can be transmitted, via radio frequency signals, to a remote RF receiver coupled to a video monitor or other output device. The endoscopic camera is adapted to receive a variety of adapters and probes, depending upon the desired procedure.

In one embodiment, the hand-held portable endoscopic camera of the present invention includes a lens means for (i) emitting light translated from a light source means through a fiber bundle to illuminate an object positioned adjacent the lens means; and (ii) for translating an image of the object from the lens means to the video imaging means. A coupling means optically couples the lens means to a video imaging means. The video imaging means converts the image of the object into video signals. The video imaging means then outputs the video signals to a display means where the practitioner views the illuminated object.

Also as discussed in detail below, a power supply means supplies electrical power both to the light source means, the video imaging means, and optionally, to a display means, and a transmitter means. In one embodiment, a first hand-held housing means houses the lens means, video imaging means, light source means, power supply means, and optionally, additional components including the display means, and/or transmitter means, such that the camera is convenient to manipulate. This first housing means allows the practitioner to inspect a variety of objects without using cumbersome cords and cables. As will be discussed in detail, a variety of additional components are connected to or mounted integrally within the hand-held housing means.

Optionally, a second housing means is employed to house a battery, for example, decreasing the weight of the first housing means. In one embodiment, the portable self-contained camera is comprised of (i) first and second housing means; (ii) components attached within or on the first housing means; (iii) components attached within or on the second housing means; and (iv) means for electrically coupling the components within or on the first and second housing means, such as at least one cable, cord or wire.

Different embodiments of cameras of the invention are disclosed in FIGS. 1–7, 8–9, 10–11, 16–22, 26–31, and 32. A variety of the components of the cameras in these embodiments are interchangeable between embodiments, as will be appreciated by one skilled in the art.

Examples of the lens means of the present invention will first be described in detail, after which examples of the light source means will be described. Examples of the video imaging means is then described, followed by examples of the power supply means. Various additional components will then be discussed, including the display means, transmitter means, sleeve means, housing means, adapter means, probe means and kit. An example of a wiring diagram for each of the embodiments disclosed herein is also disclosed.

B. The Lens System

With reference now to FIGS. 1–4, one embodiment of the invention is the self contained, hand-held, portable endoscopic camera 10. As will be discussed in detail below, camera 10 contains all of the elements necessary for a practitioner, with a single hand, to orient a probe means in a patient's ear for example, and view the contents of the ear in a display means without cumbersome use of external cables. All of this is accomplished without having to look a significant distance away from the ear in order to view the display means and without being limited to a certain office or space. The practitioner is free to move about the patient, or to a different office, and is able to use the practitioner's free hand to otherwise assist in the procedure.

Figure 3:
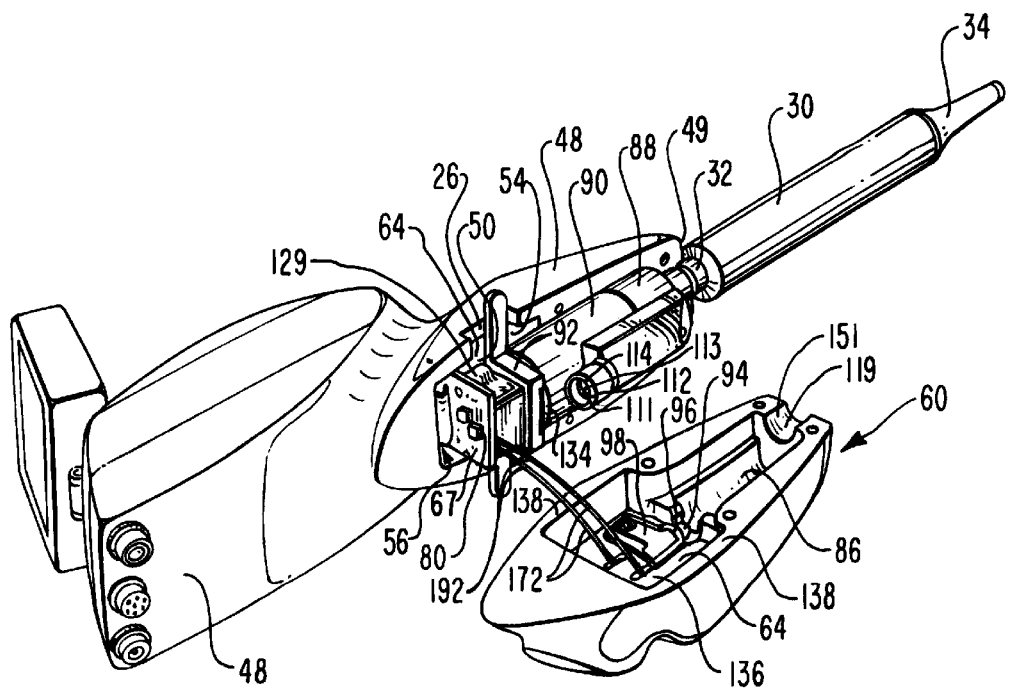
FIG. 3 is a perspective view of the portable endoscopic camera of FIG. 1 with the bottom of the camera housing removed.
Figure 4:
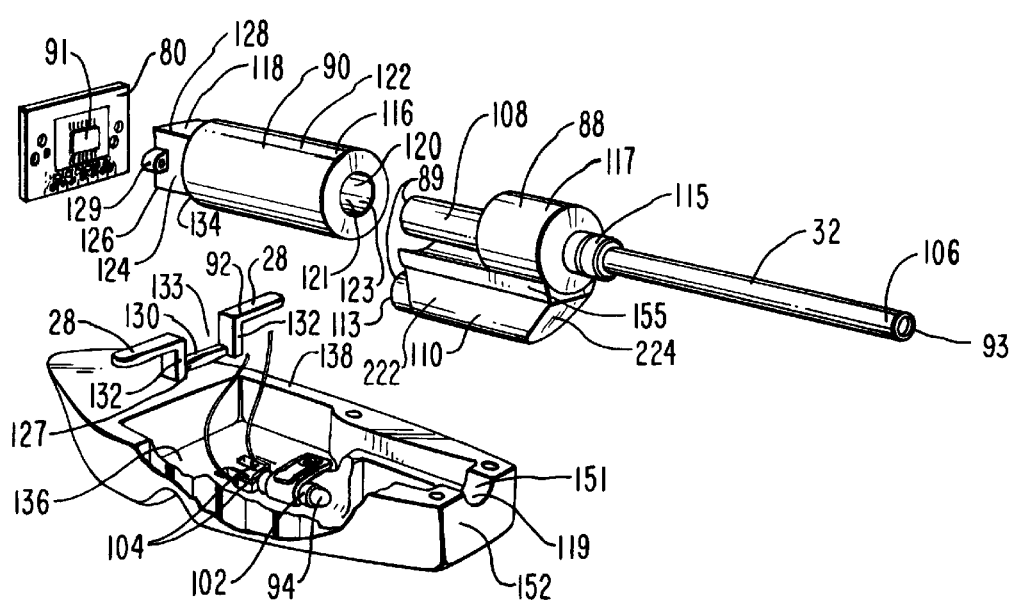
FIG. 4 is an exploded view of various components of the portable endoscopic camera of FIG. 1.

With reference now to FIGS. 3–4, in one embodiment, the lens means of camera 10 is comprised of a lens fiber module 88 having a proximal end 89 and a distal end 106. Module 88 is comprised of lens tube 32, lens tube 32 having a distal end 93, and a proximal portion 108. Module 88 further includes a distal hub 115 and a proximal hub 117. A fiber light input port 110 on proximal end 89 of module 88 houses a fiber bundle 112. Fiber light input port 110 includes a proximally extending cylindrical collar 113 adjacent fiber bundle 112. The inner diameter of collar 113 is the same or slightly larger than the outer diameter of fiber bundle 112. Collar 113 includes a proximal edge 111, the proximal edge 111 of collar 113 defining a proximal input port face 114.

Upon entering lens tube 32 from input port 110, fiber bundle 112 disperses into fibers along the longitudinal axis of lens tube 32. As will be discussed in detail below, input port 110 is optically coupled to the light source means for translating light from the light source means to the distal end of the lens tube 32. Light from the light source means travels into input port 110 and through the fibers in lens tube 32 to distal end 93 of lens tube 32 where the translated light is emitted from distal end 93, illuminating an object when distal end 32 is positioned adjacent the object. As will be discussed in further detail below, proximal portion 108 of lens tube 32 is optically coupled to the video imaging means for translating an image of the illuminated object from the distal end 93 of the lens tube 32 to the video imaging means.

By way of example, in one embodiment the lens fiber module 88 is the lens fiber module of endoscopic assembly M-150 manufactured by Cuda Products Corporation, Jacksonville Fla. The efficiency of module 88 is improved by polishing the finish of fiber bundle 112.

Figure 26:
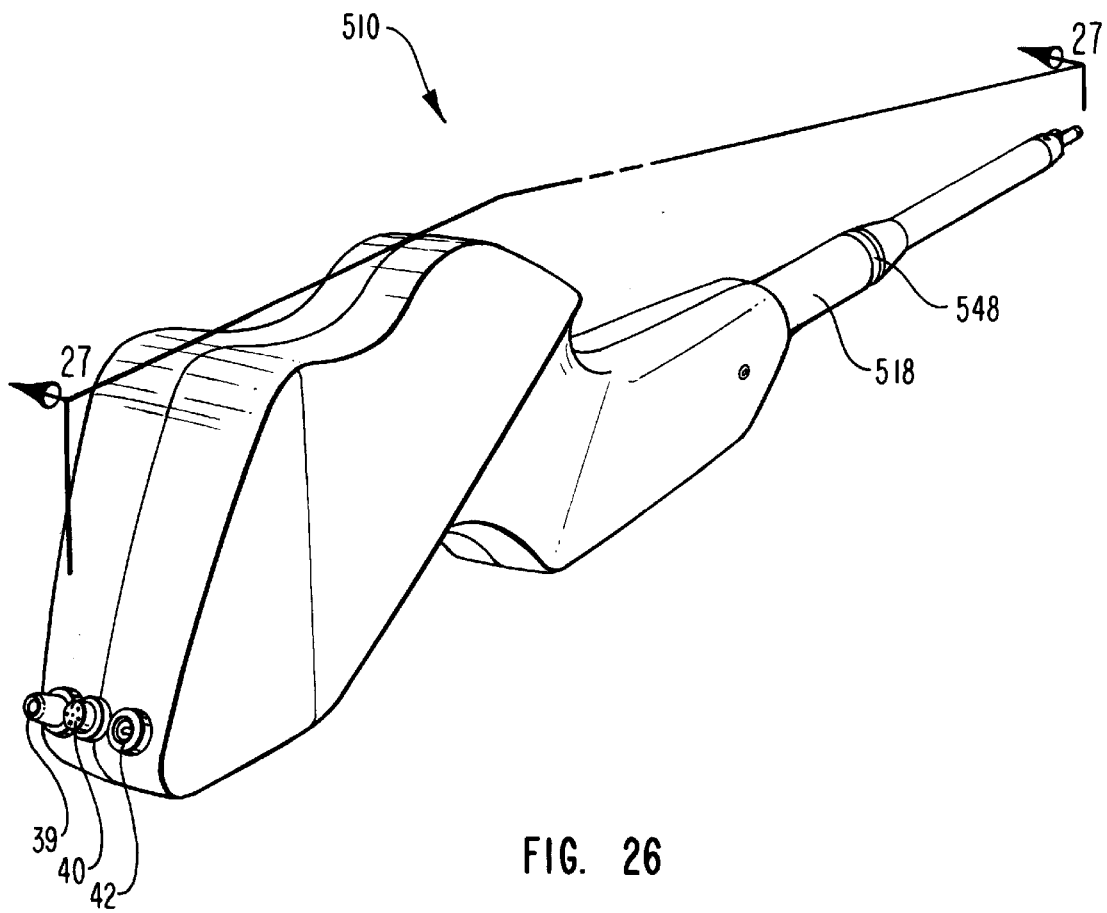
FIG. 26 is a perspective view of another embodiment of a portable endoscopic camera.
Figure 26A:
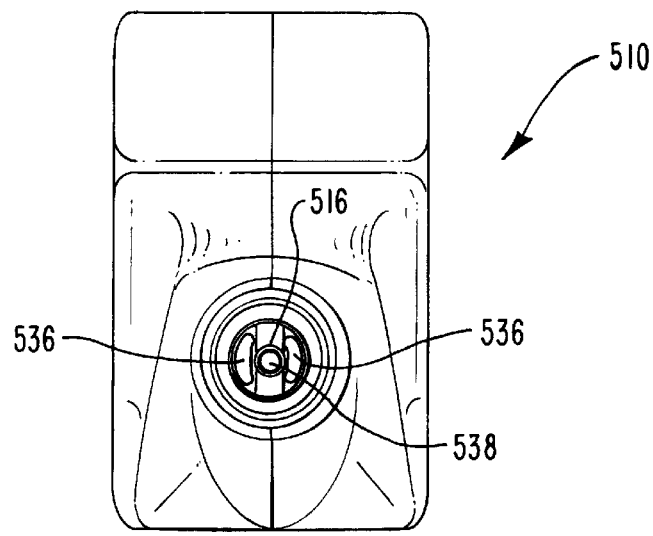
FIG. 26a is a front view of the camera of FIG. 26.
Figures 26B, 27:
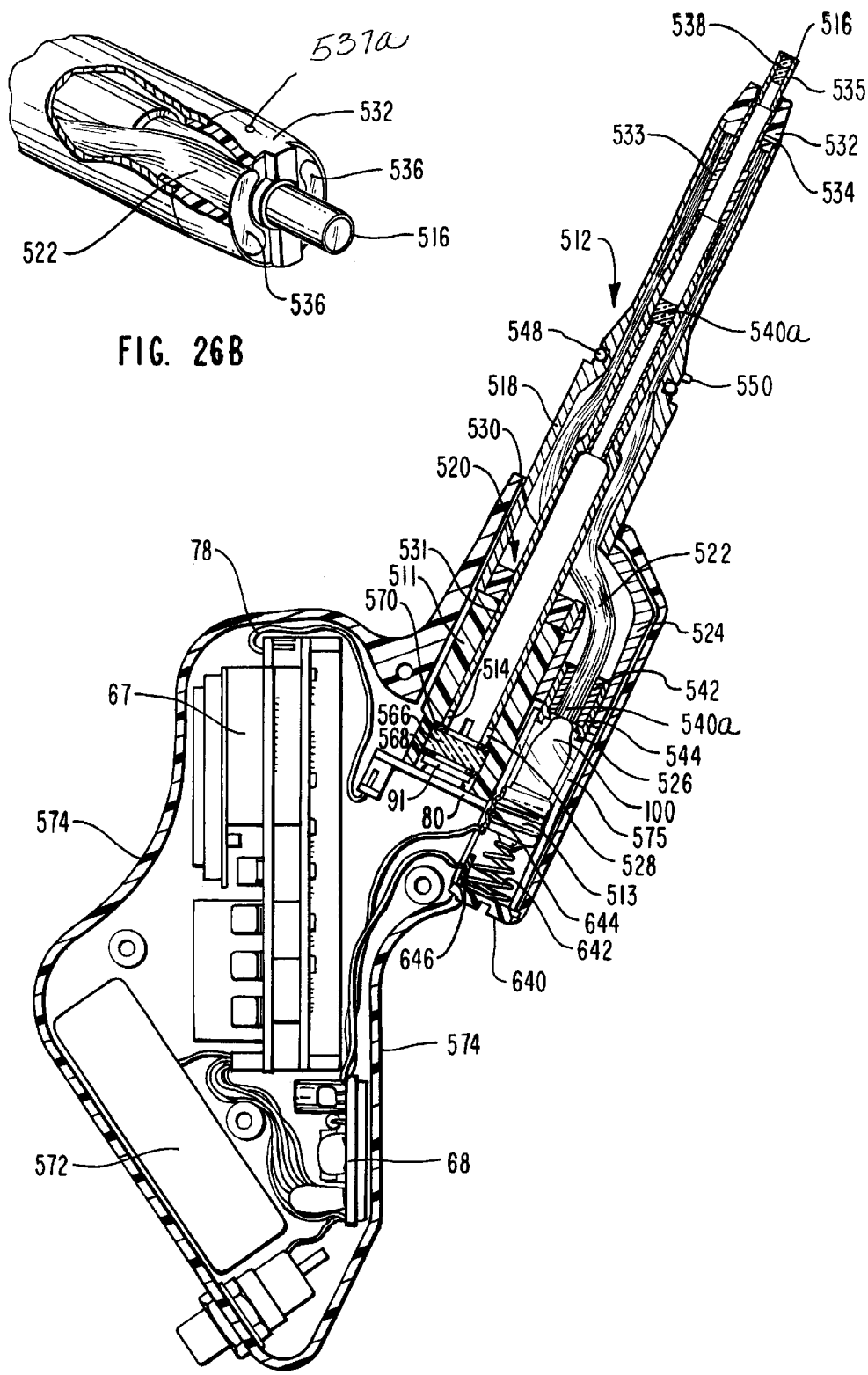
FIG. 26b is a perspective cut away view of an embodiment of a distal tip of the camera of FIG. 26.
FIG. 27 is a cross-sectional view of the camera of FIG. 26.

Self-contained camera 510 of FIG. 26 also includes a lens fiber module 512, as shown in FIG. 27. Lens fiber module 512 includes a proximal end 514, a distal end 516, a housing 518, a lens train 520, a series of optical glass fibers 522, and a fiber light input port 524. Proximal end 514 of module 512 includes the proximal end 526 of the fiber light input port 524 and the proximal end 528 of lens train 520.

As shown in FIGS. 26b and 27, lens train 520 includes a lens tube 530 having a proximal end 528 and a distal end 516. In one embodiment, lens tube 530 is comprised of three finely threaded tubular components, a proximal tube 531, an intermediate tube 533, and a distal tube 535. A lens tube guide 532 maintains distal end 516 of lens tube 530 in a desired, fixed position within lens train housing 518. An orientation post 534 may be employed to assist in properly orienting lens tube guide 532. In one embodiment, as shown in FIG. 26b, a set screw 537a may be disposed through the lens tube guide 532 to secure distal tube 535 in a desired position.

In one embodiment, lens train 520 is prefocused, such that the practitioner is not required to focus lens train. In another embodiment, a focusing means for focusing the translated image of the object is provided. For example, it is possible to twist distal tube 535 within intermediate tube 533, thereby adjusting the focus of the lens train 520. In yet another embodiment, it is possible to employ a focus wheel (not shown) engaging threads (not shown) on proximal tube 531 to adjust the focus of lens train 520.

Lens train 520 includes a series of finely annealed, high grade optical lenses disposed therein. In one embodiment, the lenses include a distal objective lens assembly 538 disposed within distal tube 535. By way of example, objective lens assembly 538 may comprise a plurality of packed lenses. An achromatic relay lens 540a is disposed within the proximal tube 531. In one embodiment, each of the objective and relay lenses are achromatic, such that they compensate for distortions in color. In one embodiment, the distal lens assembly comprises a projection lens while the proximal lens comprises a condenser lens.

At a proximal end thereof, fibers 522 include an epoxied fiber bundle 540 surrounded by an inner collar 542 which is surrounded by collar 544 of fiber light input port 524. Bundle 540 may be polished to enhance light input. Collar 544 extends proximally such that bulb 100 can be disposed within collar 544 and abutted against the proximal portion of the fiber bundle 540, as shown in FIG. 27.

In a preferred embodiment, fiber bundle 540 travels through input port 524, then bifurcates within housing 518. Upon bifurcating, one portion of fibers 522 proceeds on one side of the lens train, while another portion proceeds on the other side of a lens train. Each bifurcated portion of fiber bundle 540 then proceeds longitudinally along the shaft within lens fiber module 512 until extending through the distal end of lens tube guide 532, as shown in FIG. 26b. The distal face 536 of each of the respective bundled fiber portions is shown in FIG. 26A. Light from bulb 100 exits from the distal faces 536.

Thus, lens fiber assembly 512 is optically coupled at its proximal end 514 to the light source means for translating light from the light source means to the distal end 516 of the lens means and for emitting the translated light from the distal end 516 of the lens means so as to illuminate the object when the distal end 516 of the lens means is positioned adjacent the object.

In yet another embodiment, the distal end of fibers 522 surrounds the entire periphery of the distal portion of the lens train in a circular fashion. In yet another embodiment, the distal end of the optical fibers surrounds the entire periphery of the distal portion of the lens train or is otherwise coupled to the distal portion of the lens tube, while the proximal end of the optical fibers is separate from the proximal end of the lens tube, rather than being coupled thereto.

Figure 32:
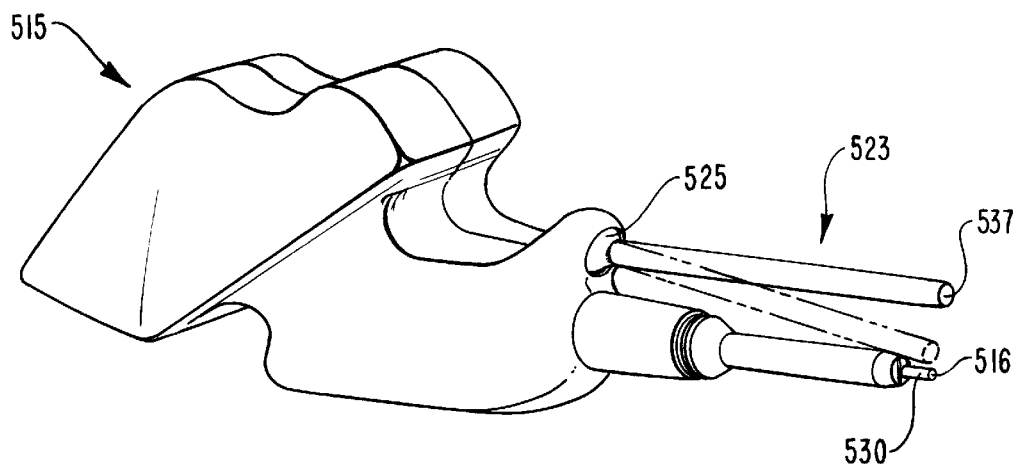
FIG. 32 is a perspective view of a another embodiment of a portable endoscopic camera.

Also as shown in FIG. 32, it is possible to provide an endoscopic camera, wherein the light source is separate from both the proximal end 514 and distal end 516 of the lens tube 530. As shown in the embodiment of the portable endoscopic apparatus 515 of FIG. 32, an illumination tube 523, which is separate from the lens train, contains optical fibers for illuminating an object through a distal end 537 thereof. A light source means is coupled to the proximal end of illumination tube 523. Tube 523 is pivotally coupled to the first housing of camera 515 through the use of a ball and socket joint 525, for example.

C. The Light Source

As indicated above, in one embodiment, the lens means is optically coupled at its proximal end to the light source means. The purpose of the light source means is for producing light for illumination of the object. A variety of examples of light source means may be employed in the present invention.

In one embodiment of the present invention, the light source means is a low wattage light source means. The low wattage light source means preferably comprises a low wattage light bulb. The phrase "low wattage" as used throughout this specification and the appended claims relates to a wattage in the range of about 0.5 watts to about 30 watts, preferably, about 0.5 watts to about 15 watts, more preferably about 0.5 watts to about 5 watts, more preferably about 1 watt to about 5 watts, most preferably, about 1.4 watts. The low wattage bulb allows the practitioner to introduce adequate light into the lens fiber module without employing a fan or a heat sink, thereby providing portability and a lightweight design.

In one embodiment, a miniature incandescent lamp or other light source is disposed within the same first housing means in which the lens means is disposed. In another embodiment, the external light source means, such as a halogen bulb or other light bulb, is enclosed within a secondary housing means, such as second housing 201 (FIG. 8) of camera 200 or second housing 608 (FIG. 30) of camera 510 coupled to the first housing means, as discussed below.

For example, it will be appreciated that it is possible to place a high wattage bulb, or in other words, a bulb having a wattage of more than about 30 watts, in a second housing means, such as second housing 608 or second housing 201, and direct the light through an optical fiber assembly into lens fiber module 88.

Figure 5:
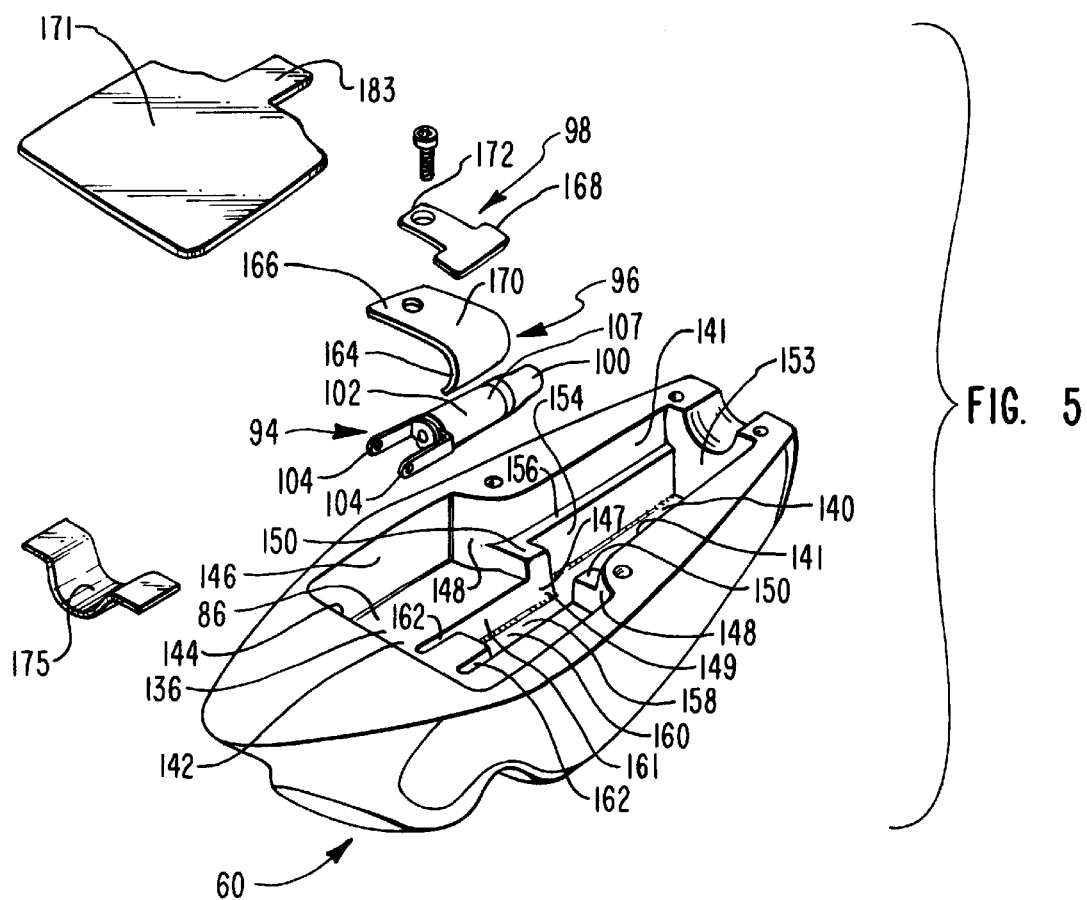
FIG. 5 is a view of the interior surface of the bottom lid and an exploded view of the lamp assembly, harness, clamp, and further including a lid and strap employed in an alternate embodiment of the portable endoscopic camera of FIG. 1.

In one embodiment of a light source means, as shown in FIGS. 3–5, an incandescent lamp assembly 94 comprises a bulb 100 and a base 443 (see FIG. 18) preferably disposed within a socket 102, socket 102 having feet 104. In one embodiment, a proximal portion of lamp assembly 94 comprises feet 104.

Preferably, a distal portion of lamp assembly 94, such as bulb 100, is disposed through input port face 114 of collar 113, such that bulb 100 is disposed directly against fiber bundle 112, providing a more efficient design by concentrating more light directly into fiber bundle 112. In one embodiment, the distal portion of lamp assembly 94 comprises bulb 100.

In another embodiment, the distal portion of lamp assembly 94 comprises bulb 100 and a portion of socket 102 distal from feet 104. By disposing socket 102 within collar 113 along with bulb 100, additional light is concentrated into fiber bundle 112. In one embodiment, it is convenient to refer to an intermediate portion as a portion of lamp assembly 94 proximal to the portion of lamp assembly 94 disposed through input port face 114, yet distal to feet 104. For example, in one embodiment, wherein only bulb 100 is disposed through input port face 114, the portion of socket 102 distal to feet 104, yet proximal to bulb 100, is an intermediate portion.

In another embodiment, the outer diameter of bulb 100 is approximately the same as the outer diameter of fiber bundle 112. A bulb having a greater diameter is less efficient, concentrating less light into fiber bundle 112. The discussion below relating to the housing means will provide a variety of examples of means for retaining the light source means in an abutting relationship with the lens means.

In a preferred embodiment, bulb 100 includes means for concentrating the illumination of the light emitted by bulb 100. Examples of the concentrating means include a lens disposed on or within bulb 100, such as a focused end lens. Light sources which are preferred in the present embodiment include krypton and incandescent bulbs.

Because of the configuration of the invention, bulbs as small as flashlight bulbs may be used in the present invention, a significant advance within the art. By way of example, one presently preferred light source means is a K-222 Krypton flashlight lamp having a focused end lens, an amperage of 0.6 amps, and a recommended voltage of approximately 2.33 volts.

With the low wattage light source means developed herein, it is possible to achieve the resolution achieved by a video imaging means having a halogen bulb light source of 50 watts or more, while employing a light bulb which emits significantly less heat. Moreover, the color of the image is not distorted, as with certain high wattage systems.

D. The Video Camera

As indicated above, the lens means is optically coupled to the video imaging means for translating an image of the illuminated object from the distal end of the lens means to the video imaging means. The video imaging means is comprised of a (i) sensor array coupled to the lens means and (ii) conversion means, electrically coupled to the sensor array, for converting images translated by the lens means and impinging upon said sensor array into video signals, and for outputting the converted video signals.

Figure 2:
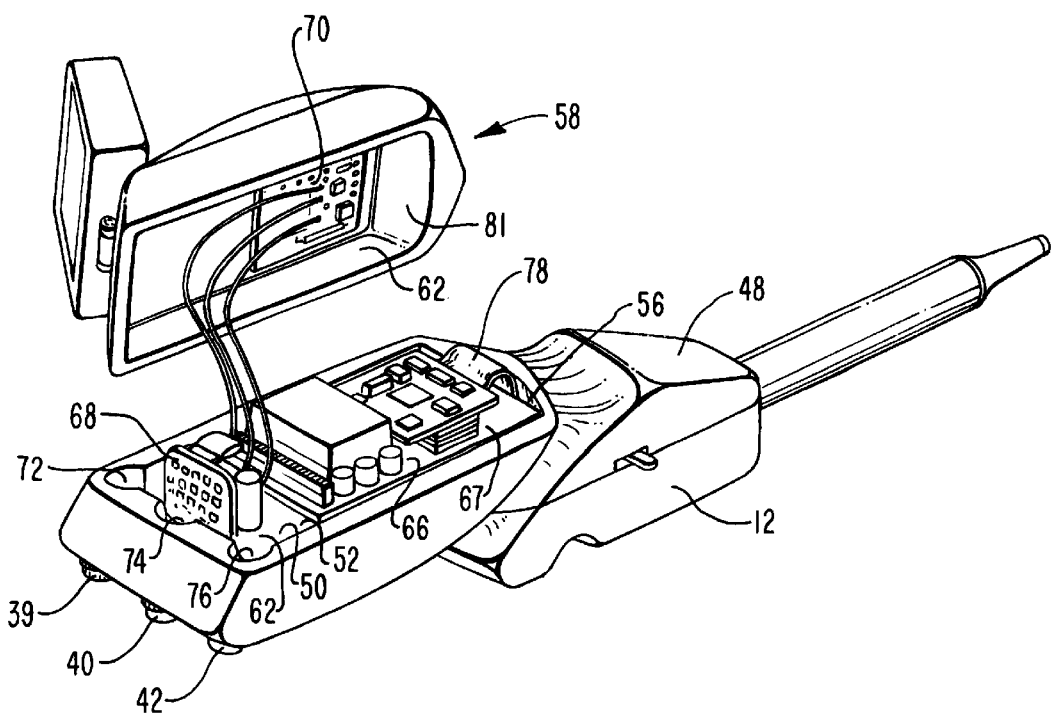
FIG. 2 is a perspective view of the portable endoscopic camera of FIG. 1 with the top of the camera housing removed.

By way of example, one presently preferred embodiment of a video imaging means is a camera assembly 67 as shown in FIGS. 2–4. Camera assembly 67 has a plurality of vertically stacked printed circuit boards 66 attached by a ribbon cable 78 to a CCD array circuit board 80. By vertically stacking the printed circuit boards 66, camera assembly 67 is able to fit more readily in a hand-held housing means. CCD printed circuit board 80 of camera assembly 67 includes a CCD sensor array 91 coupled to the proximal end of the lens means. Camera assembly 67 further comprises a blue lens 400, shown in FIG. 18, for enhanced color resolution.

An example of a preferred video imaging means is a camera assembly 67 comprised of a KST-90 CCD camera assembly, available from KOWA Optimed, Inc. Torrance, Calif. In yet another embodiment, the apparatus disclosed herein has the capability of digitally storing video images.

E. The Optical Coupler

The invention further comprises a means for optically coupling the lens means to the video imaging means. For example, as shown in FIGS. 34, optical coupler 90 is provided to couple an image under examination from lens tube 32 into CCD array 91 on CCD array printed circuit board 80. Coupler 90 includes a housing having a distal end 116 and a proximal end 118. The housing of coupler 90 further has an interior surface 120 defining a passageway 121 and an exterior surface 122 defining a cylinder at distal end 116 and a square-shape at proximal end 118.

Square-shaped proximal end 118 of exterior surface 122 of coupler 90 includes opposing parallel side walls 124, each of which are perpendicular to a bottom wall 126. Attachment members 129 affix proximal end 118 of coupler 90 to CCD array circuit board 80, through the use of screws for example. The proximal end (not shown) of passageway 121 surrounds CCD array 91 while the distal end 123 of passageway 121 slidably surrounds proximal portion 108 of lens tube 32. Coupler 90 thus completely encloses CCD array 91 and proximal end 108, preventing stray light from corrupting the image received by CCD array 91 from lens tube 32.

With continued reference to FIGS. 3–4, as an additional aspect, the invention further includes focusing means, coupled to the sensor array, for focusing the translated image of the object onto the sensor array by adjusting the distance separating the sensor array and the proximal end of the lens means. In one embodiment, the focusing means is configured to receive the means for optically coupling the lens tube to the video imaging means. An example of this embodiment of a focusing means includes focusing bridge 92.

Focus bridge 92 features a U-shaped member including a beam 130, beam 130 having a horizontal axis. A pair of support members 132 extend vertically upward with respect to the horizontal axis of beam 130 from opposing ends of beam 130. Beam 130 and support members 132 define a U-shaped channel 133. Each support member 132 includes a flange 28 extending outwardly with respect to the U-shaped channel from the respective support member 132, each flange 28 parallel to the horizontal axis of beam 130. U-shaped channel 133 of focus bridge 92 is thus configured to receive square-shaped proximal end 118 of exterior surface 122 of optical coupler 90.

Distal face 127 of beam 130 may be notched to allow it to mate with proximal cylindrical face 134 of optical coupler 90. In the preferred embodiment, support members 132 of focus bridge 92 are disposed distal to attachment members 129 of optical coupler 90. Thus, optical coupler 90 fits within U-shaped channel 133 of focus bridge 92 such that support members 132 are disposed snugly between attachment members 129 and face 134.

It will be appreciated that in one embodiment, beam 130 of focus bridge 92 is disposed against bottom wall 126, focus bridge 92 cradling optical coupler 90, as shown in FIG. 3. Focus bridge 92 thus assists in preventing movement laterally and in a vertical plane and in maintaining optical coupler 90 along the longitudinal axis of lens tube 32. It will also be appreciated from the foregoing description that, in an alternative embodiment, beam 130 of focus bridge is disposed against top wall 128, side walls 124 being perpendicular to top wall 128.

As focus bridge 92 is positioned back and forth, interior surface 120 of distal end 116 of optical coupler 90 slides back and forth on proximal portion 108 of lens tube 32. As discussed previously, CCD array circuit board 90 is affixed to proximal end 118 of optical coupler 90, while distal end 116 of interior surface 120 of optical coupler 90 slidably surrounds proximal portion 108 of lens tube 32. Thus, selective positioning of focus bridge 92 selectively positions CCD array 91 with respect to lens tube 32.

In one embodiment, coupler 90 further includes light reflecting means for reflecting light emanating from lens tube 32 into sensor array 91. In one embodiment, the light reflecting means includes interior surface 120, or at least a portion thereof, being comprised of a light reflective material, such as chrome, aluminum, ceramic, translucent elastomer, or another material having a reflective pigment, such as a light gray or white material. In another embodiment, the reflecting means comprises coupler 90, or at least a portion thereof, being comprised of a light reflective material, such as chrome, aluminum, ceramic, translucent elastomer, or another material having a reflective pigment, such as a light gray or white material.

Figure 18:
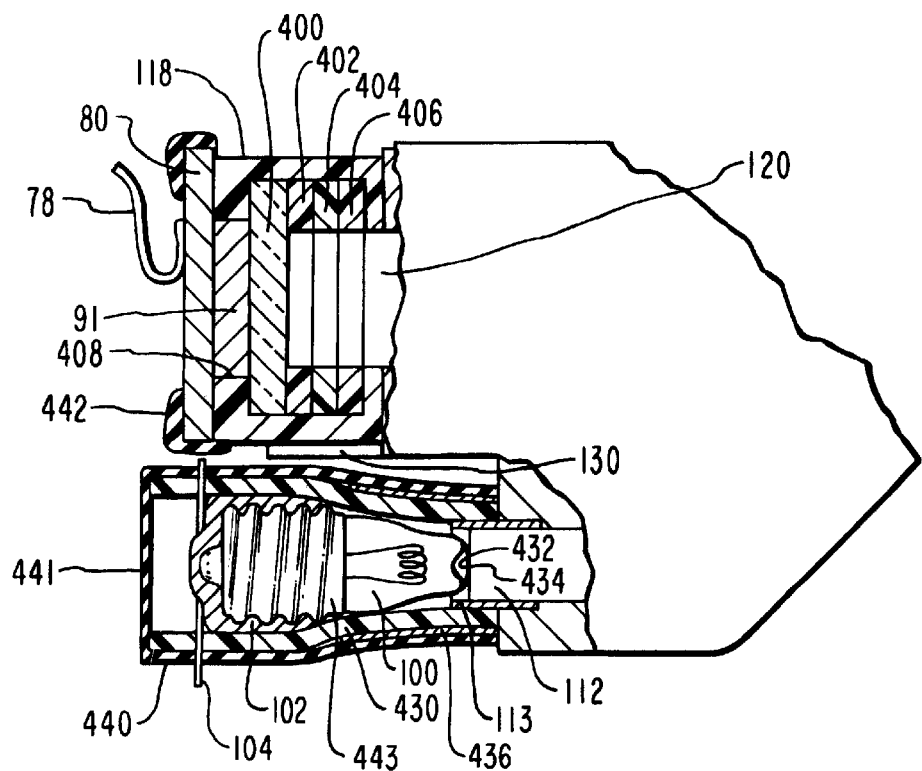
FIG. 18 is a break away view of the light source means, collar, and optical coupler of the portable endoscopic camera of FIG. 16.

In another embodiment, as shown in FIG. 18, a blue lens 400 is disposed distal to sensor array 91 within coupler 90, thereby enhancing color resolution. To further enhance resolution of the image, the invention further comprises reflecting means disposed adjacent the blue lens for reflecting light into sensor array 91. For example, the reflecting means shown in FIG. 18 is comprised of a first white washer 402 disposed against the blue lens, a second white washer 404 disposed against the first white washer 402. A black washer 406 is disposed against the second white washer 404 to properly orient washer 404 within coupler 90. Hollow washers 402, 404, 406 are disposed within the square shaped proximal portion 118 of coupler 90. Washers 402, 404, and 406 may be square shaped, rectangular, or circular in shape, depending on the configuration of interior surface 120 of coupler 90. The placement of washers 402, 404 directly adjacent the blue lens reflects light into blue lens 400 and sensor array 91. Optionally washers 402, 404 are made from a translucent elastomeric material. Washers 402, 404 may be colorless, for example.

Also as shown in the embodiment of FIG. 18, proximal end 118 of coupler 90 includes an aperture 408 for reception of sensor array 91, such that sensor array 91 is disposed directly against blue lens 400.

In yet another embodiment, as shown in FIG. 27, optical coupler 511 couples proximal end 514 lens of fiber module 512 to CCD board 80. First and second pins may be inserted within coupler 511 and the proximal portion of housing 518 of lens-fiber module 512 to maintain the coupling between lens fiber module 518 and CCD board 80.

As shown in FIG. 27, in this embodiment, rather than being disposed directly against sensor array 91, blue lens 566 is sandwiched by a proximal washer 568 and a distal washer 570. The proximal washer 568 is disposed against the sensor array 91 on CCD board 80, cushioning the interface between the blue lens 566 and sensor array 91.

In one embodiment, each washer features a hollow, rectangular shape and is formed from an elastomeric material, such as nylon. The washers may exhibit a translucent appearance, such as a colorless appearance or may feature a white color. This dynamic of sandwiching blue lens 566 between washers 568 and 570 creates a cushioning effect for the blue lens 566 and a reflective dynamic, reflecting additional light into sensor array 91.

F. The Power Supply

Examples of the power supply means will now be discussed with reference to FIG. 1. In this embodiment, the video imaging means, light source means, transmitter means, and display means are electrically coupled to and receive electrical power from a power supply means. By way of example, with reference to FIG. 1, in one embodiment, a rechargeable battery pack 35, possibly including a Nicad cell, is disposed on the first housing means to act as a power supply means. Battery pack 35 is similar to the battery pack of a cellular phone, for example. Disposable batteries or a rechargeable acid lead cell are additional examples of power supply means. The invention also includes a means for regulating the voltage produced by the power supply means, such as a voltage regulator printed circuit board 68.

Camera 10 is selectively operable in a cordless and cord-operated mode. It will be appreciated that the term "cordless" as used throughout this specification and the appended claims refers to a camera which does not have an external cord, cable or wire extending externally from the first housing for attachment to a power supply means, light source means, display means or other mechanism which is not contained within or disposed on the first housing. An example of camera 10 in the cordless mode is currently demonstrated in FIG. 1.

If cordless, battery operated power is not desirable, the operator may selectively employ power outlet supply port 39 for connecting to cord-operated power as power supply means. It will also be appreciated that the phrase "cord-operated," as used throughout this specification and the appended claims, refers to a camera which employs at least one cord, cable or wire for attachment to a fixed mechanism. Examples of a fixed mechanism include a monitor or light source permanently mounted to a wall, or a power outlet mounted to a wall or a floor.

As one example of a cord-operated power supply, if battery use is not desired, it is possible to power camera 10 with power from a permanent, wall mounted electrical outlet by using a transformer, such as a 12 volt output wall plug transformer. Camera 10 is thus selectively operable in a cordless and a cord-operated mode.

It will be appreciated that the term "self-contained" as used throughout this specification and the appended claims refers to a camera which is operable independently from a fixed mechanism, such as a wall mounted power outlet or a monitor permanently mounted to a wall.

Examples of a self-contained camera include (i) a camera which is cordless; and (ii) a camera having a first housing means and at least one portable component external to and not attached to the first housing means, wherein a cable, cord, or wire couples one or more component within or attached to the first housing means to the at least one portable component external to and not attached to the first housing means, and wherein the camera is operable without coupling any component of the camera to a fixed mechanism.

Examples of components which may be coupled to one or more component within or attached to the first housing means in the self contained camera include a transmitter means, display means, power supply means, and the light source means, which may be contained in a second housing means, such as second housing 202 or 608 discussed below, for instance. Examples of self-contained cameras include cameras 10, 200, 220, 414, 510, and 515 featured in FIGS. 1–32.

G. The Video Display

Various examples of display means will now be discussed. In one embodiment, the video signal produced within the video imaging means is output through the conversion means to an integral display means mounted on or within the first or second housing means, the display means electrically coupled to the video imaging means for displaying video images of the object. One example of a such a display means is monitor 36, shown in FIG. 1 mounted by hinge 38 on a first housing means. Monitor 36 may be demountably mounted on the first housing means such as with a dual pronged plug similar to a wall outlet plug. In another embodiment, a monitor is disposed integrally within a proximal end of the first housing means such that it can be viewed by viewing the proximal end. Monitor 36 is preferably a liquid crystal display monitor, such as Citizen LCD monitor, M329-1A, available from CBM Corporation, Japan or a similar, smaller unit. Additional examples of display means include a video monitor mounted on a wall, desk, or in a container, as discussed below, a printer, and a variety of other display means within the art.

In another embodiment, the video signal produced within the video imaging means is output through the conversion means to a separate display means, such as a wall mounted monitor, or a monitor disposed on a desk or a stand. As shown in FIGS. 1–2, the provision of S-VHS output port 40 and composite output port 42 allows portable endoscopic camera 10 to be selectively connected to one or more of such external monitors. Ports 40, 42 are electrically coupled to the video imaging means. S-VHS port 40 allows portable endoscopic camera 10 to output video signals to monitors in a variety of countries. In another embodiment, the video signal produced within the video imaging means is output through the conversion means to a monitor mounted on or within the first housing means and to a separate monitor.

In another embodiment, the video signal produced within the video imaging means is output through the conversion means to a means for recording the video images of the inspected object. For example, the installation of a memory chip within the first housing means or within a second housing means, for example, allows the practitioner to digitally record video images within the chip, then download the recorded information at a later time. Thus, free movement away from the monitor is possible without the cumbersome limitation of a cable leading to a non-portable, fixed object or mechanism.

H. The RF Transmitter/Receiver

In another embodiment, the video signal produced within the video imaging means is output through the conversion means to a transmitter means, electrically coupled to the video imaging means, for transmitting video signals generated by the video imaging means. A receiver means is designed for receiving the video signals transmitted by the transmitter means. A display means, examples of which have been previously discussed, is electrically coupled to the receiver means for displaying video images of the object.

One example of a transmitter means is signal unit 70, shown in FIG. 2. In one embodiment, signal unit 70 is a video transmitter WVT-1, available from Pragmatic Communication Systems, Inc., Sunnyvale, Calif. Also by way of example, in one embodiment, the receiver means comprises video receiver RCV915, of Pragmatic Communication Systems, Inc.

The use of the transmitter means, receiver means, and electrically coupled display means allows the operator to transmit video images from a remote location to a central monitor, for example. Thus, a clinic having a variety of rooms is not required to wire each of the rooms for endoscopic capability.

As another example of a transmitting means, as shown in FIG. 27, an RF transmitter housing 572 is disposed within first housing 574 so as to be at an angle with respect to the camera assembly 67, thereby minimizing interference between camera assembly 67 and transmitter 572. In one embodiment, transmitter housing 572 of FIG. 27 houses transmitter 70. In one embodiment, by plugging a cable into on of ports 40, 42 of camera 10, the wireless video transfer option is bypassed, allowing video transfer through the cable.

I. Wiring Diagram

Figure 7:
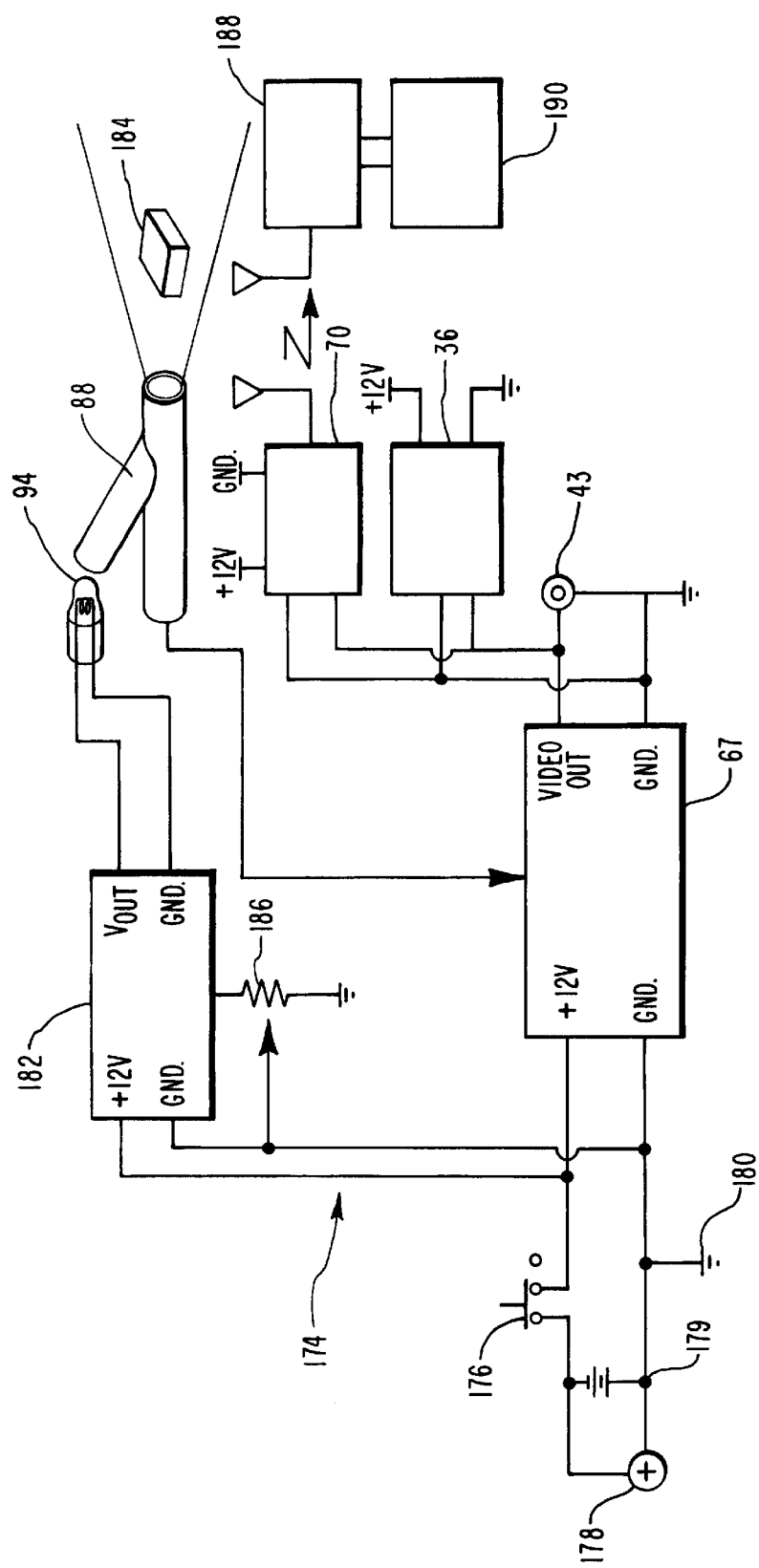
FIG. 7 is a possible wiring diagram for each of the portable endoscopic cameras disclosed herein.

FIG. 7 demonstrates an example of a wiring diagram 174 for the camera embodiments disclosed herein. Wiring diagram 174 discloses an on/off switch 176 electrically coupled to an outlet power source 178 which is electrically coupled to ground 180. Battery power source 179 is also disclosed. A power supply of 12 volts is employed in the presently preferred embodiment.

In one embodiment, power is also directed to a voltage regulator 182 for converting the power to less than about 12 volts, such as approximately 2.33 volts. It is possible to adjust the light intensity through the use of an optional potentiometer 186, which serves as an example of intensity adjustment means, electrically coupled to the light source means, for varying the intensity of the light produced by the light source means. Optional potentiometer 186 is actuated, for example through the use of a set screw disposed in first housing 12.

Lamp assembly 94 receives the reduced voltage charge and illuminates lens-fiber module 88, which, in turn illuminates an object 184 under examination. An image of object 184 is received within lens tube 32 and directed into camera assembly 67. Camera assembly 67 directs the image into one or more output ports, represented collectively by output port 43, such as a composite video output port and/or an S-VHS video output port, and/or monitor 36, and/or signal unit 70. Receiver 188 receives the video signals transmitted by signal unit 70 and is coupled to display 190, such as a wall mounted display for displaying video images of object 184. A switch may be required to alternate between composite output and S-VHS output.

In one embodiment, as shown in FIG. 3, power wires 192 connecting lamp assembly 94 to voltage regulator 68 extend through internal passageway 56 of the housing body. It will be appreciated that a variety of wiring possibilities are available to accomplish the intent of wiring diagram 174 and that one skilled in the art will understand how to wire the various components of portable endoscopic camera 10 based on disclosures made herein.

J. Sleeve Means

With reference now to FIGS. 17–19 and FIG. 27, the invention further includes sleeve means coupled to the proximal end of the lens means for concentrating light into the lens means. One example of the sleeve means is sleeve 430 which is disposed about at least a portion of the lens means and at least a portion of the light source means, directing light from the light source means into the lens means, as will be discussed in detail below. Sleeve 430 is an example of means for retaining the light source means in an abutting relationship with the lens means.

Normally, light emanating from bulb 100 dissipates upon leaving bulb 100. By abutting bulb 100 against lens fiber bundle, light from bulb 100 is concentrated into the bundle. In addition, as shown in FIG. 18, sleeve 430 captures additional light from bulb 100 and directs it in a longitudinal direction toward lens fiber bundle 112. Furthermore, sleeve 430 is preferably in a tight fitting relationship with at least a portion of lamp assembly 94 extending proximally from collar 113 and with the exterior surface of the collar 113, thereby retaining the bulb 100 in a fixed position with respect to the lens fiber module 88.

As shown in the preferred embodiment, the distal center point 432 of the bulb 100 directly abuts the proximal center point 434 of fiber bundle 112. Sleeve 430 retains bulb 100 in this concentrated, precise abutting relationship with bundle 112, intensely concentrating light from bulb 100 into bundle 112 despite any activity occurring in manufacturing or in moving or jostling the camera. In part because of the abutting relationship of the bulb and because of the use of sleeve 430, the low wattage light bulb of the present invention adequately illuminates the image to be viewed by the practitioner.

In a preferred embodiment, sleeve 430 includes reflecting means for reflecting light into the lens means. In one embodiment, the reflecting means is comprised of sleeve 430 being comprised of a high gloss material. For example, sleeve 430 may be comprised of a translucent or transparent high gloss elastomeric material, such as nylon. In one embodiment, the translucent sleeve 430 has a colorless, light pink or rose colored pigment.

Figure 19:
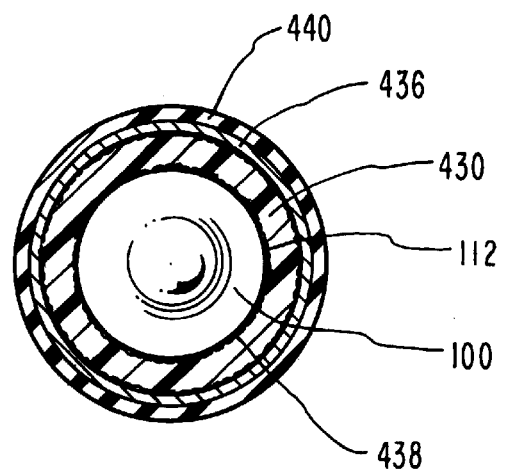
FIG. 19 is a cross sectional view of the light bulb, sleeve and other related components of the endoscopic camera shown in FIGS. 16–18.

In another embodiment, as shown in FIGS. 18 and 19, the reflecting means further comprises a light reflective material 436 disposed about the transparent or translucent sleeve 430. The reflective material 436 reflects light emanating from bulb 100 into fiber bundle 112. For example, the light reflective material 436 disposed about sleeve 430 may be in the form of aluminum, chrome, ceramic, plastic, for example, or another material having a reflective pigment such as a white pigment or a light gray pigment.

In another embodiment, the reflecting means is comprised of sleeve 430 being comprised of a light reflective material such as aluminum, chrome, plastic, translucent elastomer, ceramic, or another material having a reflective pigment such as a white pigment or a light gray pigment. In another embodiment, the reflecting means is comprised of the sleeve 430 having a reflective interior surface, such as an aluminum, chrome, ceramic or plastic interior surface or another material having a reflective pigment such as a white pigment or a light gray pigment. In yet another embodiment, the sleeve is comprised of a ceramic material having a chrome surface on the interior thereof.

Also by way of example, in one embodiment, the reflecting means is comprised of the sleeve 430 comprising ribs 438 extending longitudinally along the length of sleeve 430, as shown in FIG. 19. Ribs 438 preferably extend along the interior and exterior surface of sleeve 438. It is believed that ribs 438 act to direct light longitudinally into the fiber bundle 112.

Figure 17:
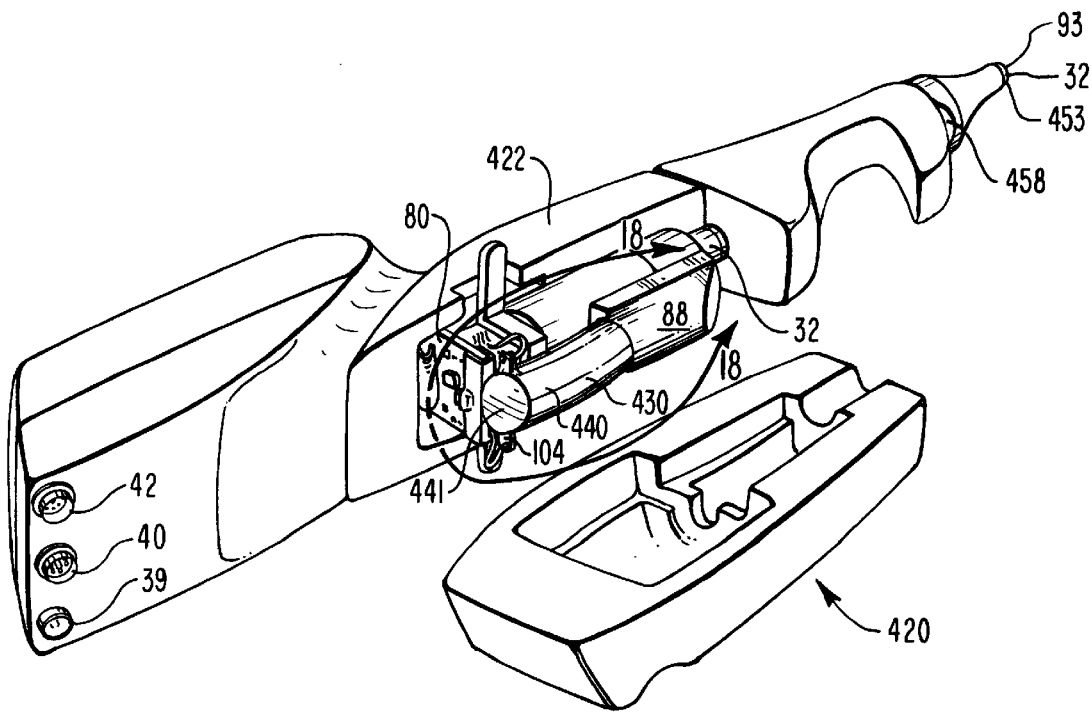
FIG. 17 is a view of the portable endoscopic camera of FIG. 16 with the bottom lid removed.

With continued reference to FIGS. 17–19, to prevent electrical damage caused by contact between bulb 100 and CCD board or other electronic assemblies, it is possible to dispose an insulator 440 about the reflective material 436 and/or sleeve 430. Insulator 440 may also be employed in the form of an adhesive to retain reflective material 436 about sleeve 430. In another embodiment, as shown in FIG. 18, insulation 442 is placed on CCD board 80. With reference to FIGS. 17 and 18, is possible to prevent interference with the CCD board 80 during movement of coupler by bending socket feet 104 of socket 102 at a right angle. In one embodiment, insulation 440 also covers feet 104 and the associated circuitry.

Figure 20:
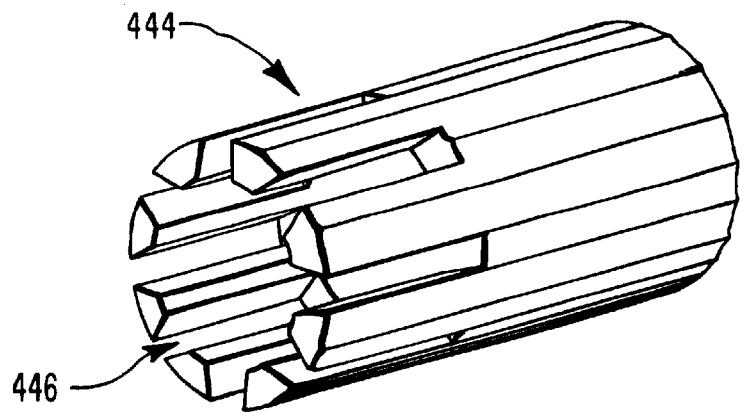
FIG. 20 is an alternate embodiment of a sleeve for use in the camera of FIG. 16.
Figure 21:
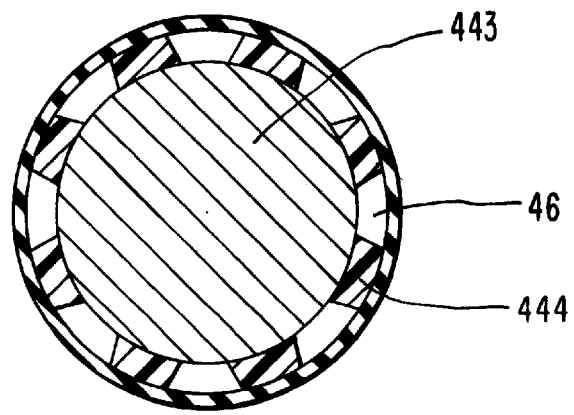
FIG. 21 is a cross sectional view of the sleeve of FIG. 20 in which the slots are disposed about the base of an incandescent light bulb.
Figure 22:
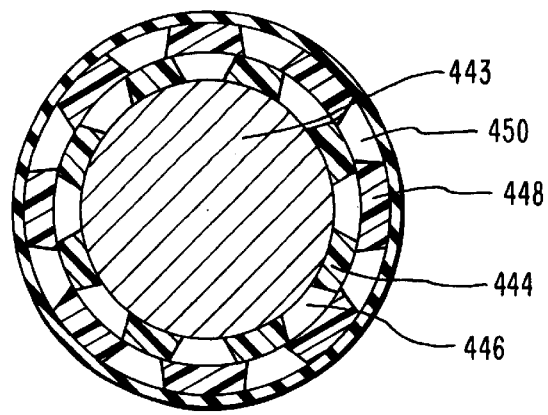
FIG. 22 is a cross sectional view of the sleeve of FIG. 21 with a second sleeve disposed about the sleeve of FIG. 21.

Various sleeve embodiments are possible. As shown in FIGS. 20 and 21, in one embodiment, if increased wattage is desired, rather than employing a heat sink or a fan, the heat is vented. Although the low wattage light bulbs used in the present invention with quality resolution emit dramatically less heat than typical endoscopic camera bulbs, venting the heat increases the life of the bulb, and decreases the chance of heating distal end 93 of lens tube 32 and the camera housing, or adversely affecting CCD circuit board 80 and other circuitry.

To vent heat, in one embodiment, sleeve 444 is comprised of venting means for venting heat from the light source means, such as slots 446. Slots 446 extend between the exterior and interior surfaces of sleeve 444. In one embodiment, rear portion 441 of insulation 440 shown in FIGS. 17 and 18 is removed and heat from the lamp assembly 94 is vented proximally through slots 446. In one embodiment, slots 446 are disposed above socket 102 and any portion of base 443 protruding from socket 102, while the non-slotted portion of sleeve 444 is disposed above bulb 100.

Figure 24:
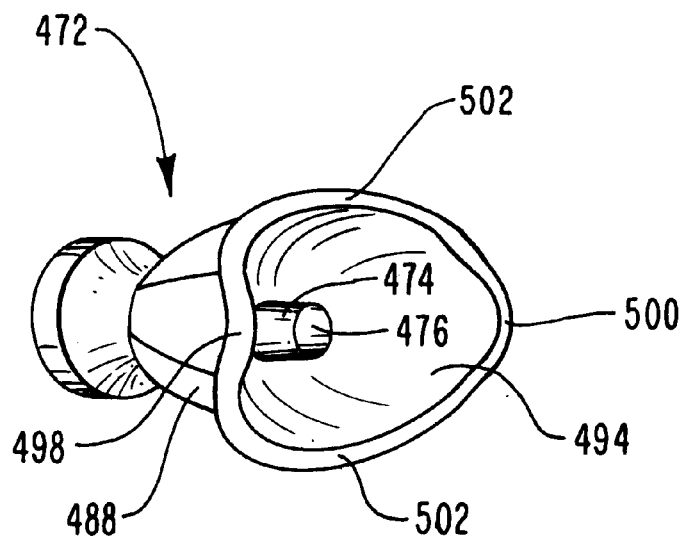
FIG. 24 is a perspective view of an optical probe.

In yet another embodiment, a dual slotted sleeve arrangement is employed as shown in FIG. 24. In this embodiment, a second sleeve 448 including venting means for venting heat from the light source means, such as slots 450 is disposed about the first sleeve 444 such that the first sleeve venting means are offset from the second sleeve venting means. In this embodiment, a sleeve effect is continuous throughout the length of the light assembly 94 even though the first and second sleeves are slotted.

The effects of increased heat can also be ameliorated without employing a heat sink or fan by moving the bulb 100 away from collar 113 and from the first housing, by perforating the area of the housing surrounding the light source means, employing a fiber glass housing or a housing comprising a plastic compound having fiberglass embedded therein, employing a housing comprising another insulative material, or by employing a means for retaining bulb in abutting relationship with the fiber bundle which does not surround the light bulb.

In another embodiment, a sleeve having a diameter approximately the same size as the diameter of collar 113 surrounds a portion of lamp assembly 94 and abuts the proximal edge 111 of collar 113, thereby coupling the sleeve to collar 113.

K. Housing Embodiments
1. First Housing Embodiment

As another aspect of the invention, various housing means will now be discussed in detail. In order to house the components of the invention, a variety of housing means are available, such as first housing 12, shown in FIG. 1. It will be appreciated that first housing 12 of FIG. 1 is an example of a first hand-held means for housing the light source means, video imaging means, lens means, and power supply means, such that the apparatus is self-contained and convenient to manipulate. In the embodiment of FIG. 1, the light source means is internal within the first housing 12.

As shown in FIG. 1, first housing 12 has an exterior surface 14, a distal end 16, a proximal end 18, a top surface 20, a bottom surface 22, and opposing sides 24. Monitor 36 is hingeably mounted on proximal end 18 of first housing 12. Battery pack 35 is disposed on top surface 20 of first housing 12. In the embodiment of FIG. 1, a probe adapter 30 projects from distal end 16 and couples lens tube 32 of module 88 to a probe 34.

First housing 12 further includes stabilizing means for stabilizing camera 10, such as gripping groove 44 and gripping slot 46, which aid the user in securely grasping camera 10. Gripping groove 44 is configured to approximate the contour of an adult hand between the thumb and forefinger, and gripping slot 46 is configured for partial insertion of the third, fourth, and/or fifth fingers during use. First housing 12 is balanced such that the practitioner can grip gripping groove 44 with the thumb and forefinger and rest a proximal portion of the bottom surface 22 on the practitioner's hand or wrist. By gripping groove 44 or other areas of the contoured housing, the practitioner is able to successfully control the direction and orientation of the endoscopic camera. Slip proof tape is also preferably disposed on the surfaces where gripping is expected.

With reference now to FIGS. 2 and 3, first housing 12 is comprised of a housing body 48 having an interior surface 50. Interior surface 50 defines a top cavity 52, a bottom cavity 54, and an internal passageway 56 linking top cavity 52 and bottom cavity 54. A segmented hollow top lid 58 covers top cavity 52 while a segmented hollow bottom lid 60 covers bottom cavity 54. Top cavity 52 and the interior surface 81 of corresponding top lid 58 define a top chamber 62, while bottom cavity 54 and the interior surface 86 of corresponding bottom lid 60 define a bottom chamber 64.

The segmentation of first housing 12 allows for an efficient use of space and weight distribution, which increases the practitioner's ability to hold and operate light-weight, hand-held portable endoscopic camera 10.

In one embodiment, first housing 12 defines a collar 119 disposed about distal hub 115 for retaining lens fiber module 88 in a fixed position with respect to first housing 12. A portion of collar 119 is defined by a recess 151 within distal end 152 of bottom lid 60 while a corresponding portion of collar 119 is defined by a recess (not shown) within the distal end 49 of housing body 48. By disposing distal hub 115 in collar 119 and proximal hub 117 proximal to collar 119, lens-fiber module 88 is engaged in an interlocking relationship with first housing 12, as shown in FIG. 3. Adding adapter 30 to lens tube 32 enhances the interlocking relationship.

With reference now to FIG. 2, top chamber 62 houses the plurality of vertically stacked printed circuit boards 66, preferably three printed circuit boards of camera assembly 67. The disposition of the vertically oriented boards 66 within top chamber 62 allows camera assembly 67 to be inserted into a thin housing. Ribbon cable 78 of camera assembly 66 extends into internal passageway 56 and attaches to CCD array printed circuit board 80 of camera assembly 67 within bottom chamber 64 (shown in FIG. 3).

With continued reference to FIG. 2, top chamber 62 also houses voltage regulator circuit board 68, signal unit 70, power supply port 39, S-VHS outlet port 40, and composite outlet port 42. Top cavity 52 includes a first proximal recess 72, a second proximal recess 74, and a third proximal recess 76 for disposition of power supply port 39, S-VHS outlet port 40, and composite outlet port 42 and their associated wiring therein, respectively. The interior surface of top lid 58 is contoured to cover the vertically stacked circuit boards 66 of camera assembly 67 and is contoured to receive signal unit 70.

As shown in FIGS. 1–3, first housing 12 further includes a pair of opposing focus adjustment slots 26 disposed within sides 24. Opposing focus adjustment flanges 28 of focus bridge 92 project from opposing adjustment slots 26 for adjusting the focus of portable endoscopic camera 10. Each slot 26 is configured in a rectangular shape to allow each flange 28 to slide in a front to rear and rear to front direction. As will be discussed in additional detail below, in one embodiment, beam 130 of focus bridge 92 is suspended within adjustment notch 136 of bottom lid 60. Opposing adjustment flanges 28 are slidably suspended on the opposing edges 138 of bottom lid 60 within opposing adjustment slots 26 of housing body 48.

Focus bridge 92 thus serves as an example of means for focusing the translated image of the object onto the sensor array by adjusting the distance separating the sensor array and the proximal end of the lens means and for maintaining the longitudinal axis of the lens means. The performance of both of these functions is a significant contribution to the art.

The lens means and the light source means are closely aligned within bottom chamber 64, which is specifically designed to fit only certain components and is separate from a variety of the other components of portable endoscopic camera 10. As a result of applicant's chambering, light from the light source means is essentially retained within a single, relatively smaller chamber, and is concentrated into the lens means.

Interior surface 86 of bottom lid 60 will now be described in detail with reference to FIGS. 5. It will be appreciated that two major goals of bottom chamber 64 are (1) to prevent the movement of the components associated closely with the light source; yet (2) permit the back and forth sliding movement of sensor array circuit board 80. In order to accomplish each of these objectives, interior surface 86 of bottom lid 60 includes a bottom lid floor 158, wide adjustment notch 136, a thinner, deeper, input port reception channel 140, bottom lid upper distal walls 141, and a lamp assembly reception channel 160.

Adjustment notch 136 is defined by an adjustment notch floor 142, a proximal wall 144, opposing side walls 146, opposing proximal ends 148 of opposing bottom lid upper distal walls 141, and the imaginary plane extending between and upwardly from the proximal faces of posts 150. However, in one embodiment, sensor array circuit board 80 is only allowed to move back and forth within a proximal portion of the adjustment notch 136.

Channel 160 is an example of a means for retaining the light source means in an abutting relationship with the lens means. Channel 160 is formed in the floor 142 of adjustment notch 136 and is configured at a distal portion to receive collar 113 of fiber light input port 110. Channel 160 is bordered at a distal end by an imaginary plane extending between the distal faces of opposing posts 150. Socket feet notches 162 of channel 160 each receive a corresponding socket foot 104, each notch 162 having a surface below the floor of adjustment notch 136, yet above the surface of channel 160.

Input port reception channel 140 is designed for reception of fiber light input port 110 of fiber-lens module 88. Channel 140 is defined by the distal end 153 of interior surface 86 of bottom lid 60 opposing input port channel side walls 154, opposing posts 150, a distal portion of lamp assembly reception channel 160 and the lower portion of the bottom lid upper distal walls 141. Ridges 156 are located slightly lower than the upper edges 155 of input port 110 as input port 110 is received in channel 140. A distal portion of channel 140 may be slightly wider than the upper edges 155, such that the upper edges 155 do not rest upon ridges 156. Alternatively, channel 140 is configured such that upper edges 155 are disposed upon ridges 156. Channel 140 is therefore another example of means for retaining the light source means in an abutting relationship with the lens means.

Opposing posts 150 extend upwardly from bottom lid floor 158. Opposing proximal side walls 161 of channel 160 extend proximally with respect to a bottom portion 147 of opposing posts 150, the inner face 149 of each bottom portion 147 serving as a distal wall of channel 160.

Fiber light input port 110 is disposed within input port reception channel 140 such that a distal portion of lamp assembly 94 is disposed through face 114 of fiber light input port 110. Thus, bulb 100 abuts fiber bundle 112 and collar 113 is disposed about the distal portion of lamp assembly 94. The disposition of a distal portion of lamp assembly 94 through input port face 114 creates a light concentrating chamber within cylindrical collar 113 for concentrating light produced by the light source means into the lens means.

In one embodiment, edge 111 of collar 113 is maintained between bottom portion 147 of posts 150. In another embodiment, edge 111, or alternatively, the entire collar 113 is disposed proximally such that it is maintained between opposing side walls 161. In both embodiments, collar 113 of input port 110 extends into channel 160.

Lamp assembly reception channel 160 and input port reception channel 140 thus combine to form a single illumination channel, which acts as a means for retaining the light source means in an abutting relationship with the lens means.

As an additional example of a means for retaining the light source means in an abutting relationship with the lens means, a harness 96 is disposed about lamp assembly 94 and, in one embodiment, is secured to floor 142 of adjustment notch 136. A curved end 164 of harness 96 is disposed about socket 102 of lamp assembly 94, maintaining lamp assembly 94 tightly within harness 96 such that lamp assembly 94 is suspended within channel 160. In one embodiment, flat end 166 of harness 96 is secured to floor 142 of adjustment notch. By suspending lamp assembly 94 away from the walls and floor of channel 160 within harness 96, heat is allowed to dissipate within channel 160.

Another example of a means for retaining the light source means in an abutting relationship with the lens means is a T-shaped harness clamp 98, which is disposed over harness 96 and secured to adjustment notch floor 142 as shown in FIG. 4, adding additional leverage to maintain lamp assembly 94 in a fixed position. Returning to FIG. 5, top portion 168 of T-shaped harness clamp 98 abuts outer surface 170 of harness 96 in mating relationship. The bottom portion 172 of T-shaped clamp 98 is secured to floor 142.

Figure 6:
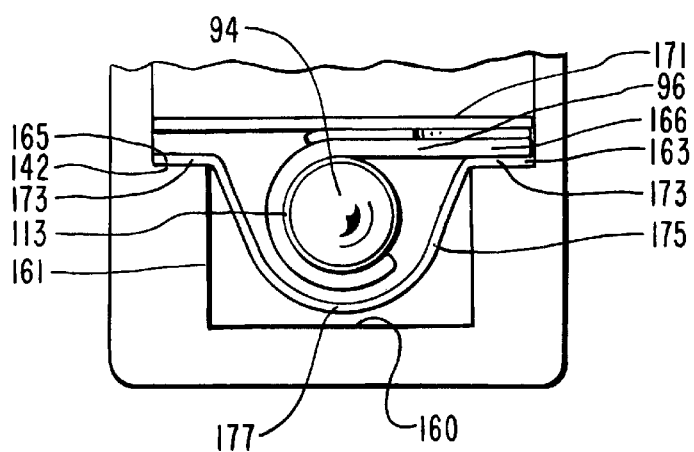
FIG. 6 is a cross-sectional view of the assembled components of FIG. 5.

In another embodiment, a flat lamp assembly lid 171 as shown in FIGS. 5 and 6 is disposed over the lamp assembly 94, forming a light concentrating chamber. FIG. 6 is a cross-sectional view in the proximal direction of an assembled FIG. 5 taken proximal to posts 150. With Lid 171 and strap 175, light is further concentrated along the longitudinal axis of lamp assembly 94 into fiber bundle 112, rather than perpendicular to the longitudinal axis and away from fiber bundle 112. By way of example, lid 171 may cover lamp assembly reception channel 160, the entire floor 142 of adjustment notch 136 or both. Optionally, lid 171 is configured with a narrow neck 183, for example, which extends between posts 150. Preferably the lid is snapped in place.

In another embodiment, as shown in FIGS. 5 and 6, the light concentrating chamber is comprised of lid 171 and a strap 175. By way of example, in one embodiment strap 175 is rectangular in shape. In another embodiment, strap 175 is square in shape. Strap 175 is made from a variety of materials such as ABS plastic and is disposed between proximal opposing side walls 161 and under at least portions of both lamp assembly 94 and collar 113.

A first upper end 163 of strap 175 is preferably attached under flat end 166 of harness 96 on adjustment notch floor 142. A second upper end 165 of strap 175 is disposed on an opposing side of floor 142 such that the distal face of opposing upper portions of strap 175 are adjacent or abut the proximal faces of posts 150. An intermediate portion 177 of strap 175 extends between ends 163 and 165.

As discussed previously, a distal portion, such as bulb 100, of lamp assembly 94 is surrounded by collar 113. Collar 113, or at least a proximal portion thereof, such as edge 111, is maintained between opposing proximal side walls 161 in channel 160 such that a distal portion of strap 175 is disposed under collar 113, or at least a proximal portion thereof. Strap 175 then also extends proximally under a portion of lamp assembly 94, such as an intermediate portion of lamp assembly 94 (e.g., the portion of socket 102 distal from feet 104). Lid 171 is disposed above lamp assembly 94 and collar 113 as shown in FIG. 6, such that light is concentrated by strap 175 and lid 171 into the lens means.

While in one embodiment, strap 175 abuts collar 113 and lamp assembly 94, in another embodiment, as shown in FIG. 6, strap 175 is disposed slightly below collar 113 and lamp assembly 94, allowing collar 113 to be disposed about the distal portion of lamp assembly 94 during manufacture.

By isolating the optics together with the light source in one chamber and the signal unit and the majority of the camera components in another chamber, damage to one chamber may be isolated to that chamber. Furthermore, a desired adjustment of lenses or light bulbs does not require an opening of the entire device. Any required maintenance is likely to occur within bottom chamber 64, allowing the components of top chamber 62 to remain uniquely housed in a relatively maintenance free environment, preventing damage to the top chamber components during maintenance.

The configuration also employs space efficiently. While the majority of top chamber 62 is oriented proximal to bottom chamber 64, a significant portion of the top chamber 62 is oriented above a significant portion of bottom chamber 64, allowing a portion of the contents of top chamber 62 to be stacked above a portion of the contents of bottom chamber 64, or in an alternative embodiment, at least allowing ribbon cable 78 to be disposed within internal passageway 56. This configuration of first housing 12 provides for a balanced orientation in the practitioner's hand. This use of space in a balanced, completely hand-held, portable endoscopic camera is a significant advance within the field.

Also in the preferred embodiment, first housing 12 includes a means for replacing the light source means. For example, in one embodiment, the means for replacing the light source means comprises a door (not shown) on bottom lid 60 for the replacement of the light bulb. The door may, for example, comprise a sliding door as typically seen in a variety of remote control devices for the replacement of batteries. In another embodiment, the means for replacing the contents of the bottom chamber comprises bottom lid 60 configured to snap off the housing body. In another embodiment, the bottom lid is spring loaded on the housing body.

Disposing lamp assembly 94 near proximal end 18 of first housing 12 within top cavity 52 behind voltage regulator circuit board 68, or near a corner recess such as 72, or 76, for example, may assist in providing access to lamp assembly 94 for maintenance thereof. A door, such as described above could be conveniently located near the lamp assembly 94. In one embodiment, this requires an extension of input port 110 or another means for coupling lamp assembly 94 to input port 110, such as a cable or a fiber bundle extending from input port 110 to lamp assembly 94.

2. Second Housing Embodiment

Figure 8:
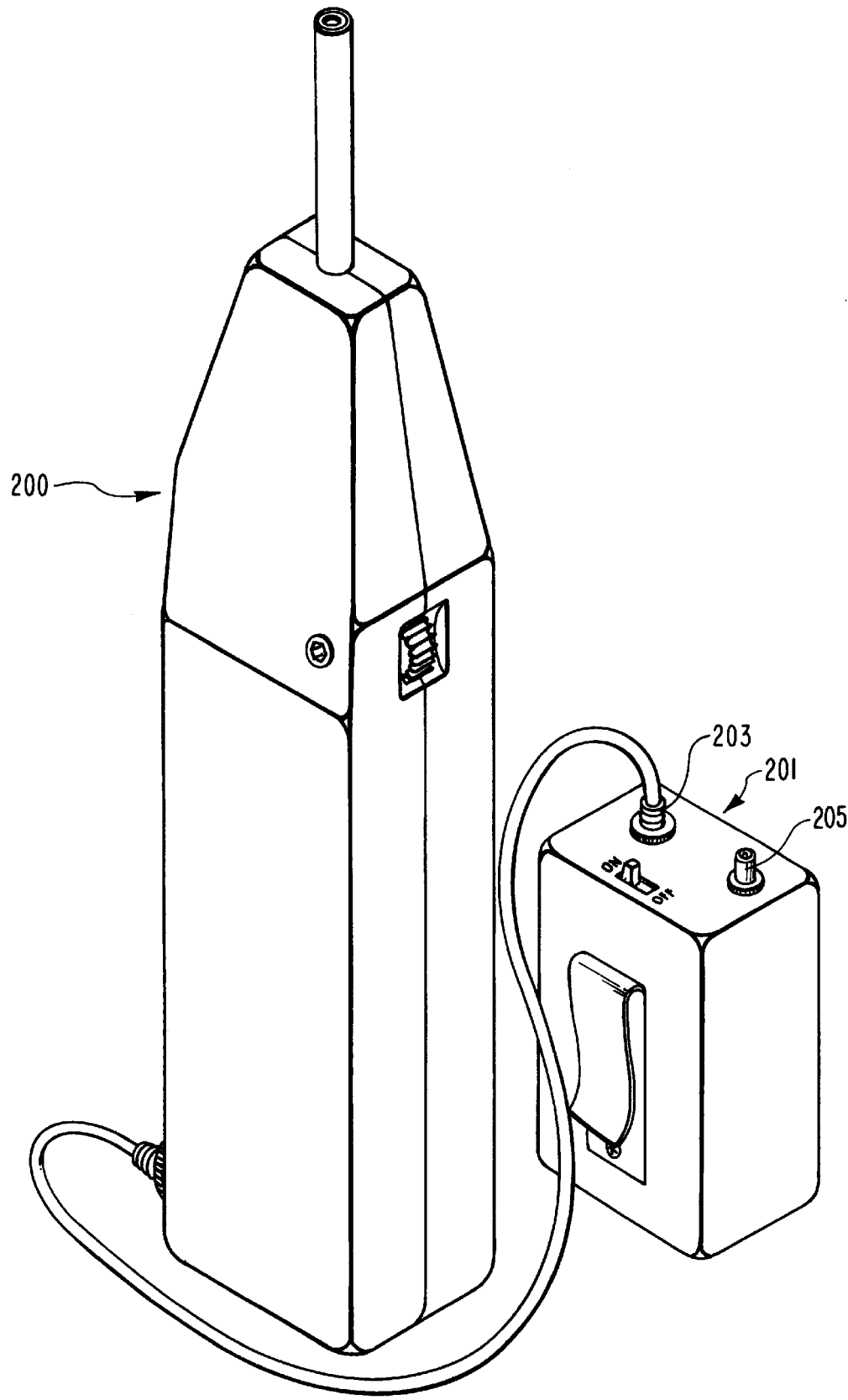
FIG. 8 is a perspective view of another embodiment of a portable endoscopic camera having a first and second housing.
Figure 9:
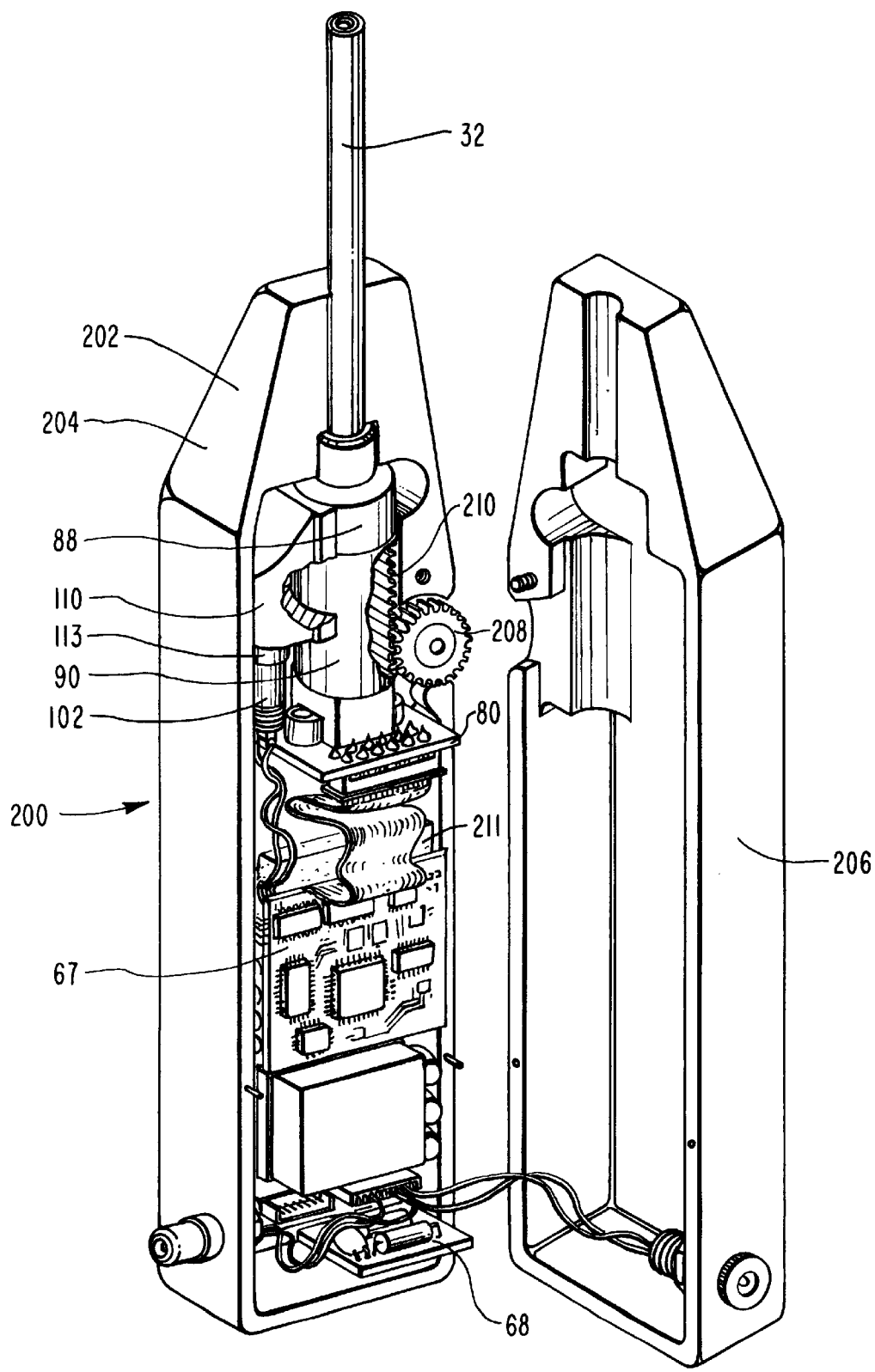
FIG. 9 is a view of the portable endoscopic camera of FIG. 8 with the lid of the first housing removed.

Another example of a portable hand-held endoscopic camera 200 is shown in FIG. 8. As shown in FIGS. 8 and 9 and as discussed previously with reference to endoscopic camera 10, portable endoscopic camera 200 includes voltage regulator circuit board 68 electrically coupled to camera assembly 67, which is coupled through coupler 90 to lens fiber module 88. Also as discussed previously with regard to portable endoscopic camera 10, bulb 100 of lamp assembly 94 directly abuts fiber bundle 112 of fiber light input port 110. Socket 102 may be surrounded by a clip or harness maintaining bulb 100 within fiber light input port 110, or the first housing 202 may be configured to retain bulb 100 within fiber light input port 110. Optionally, lamp assembly 94 may be retained within a sleeve abutting proximal edge 111 of collar 113. In one embodiment, the wiring of endoscopic camera 200 is as previously disclosed in the wiring diagram of FIG. 7.

While focus bridge 92 may be employed in this embodiment with minor adjustments, thumbwheel 208 serves as another example of means for focusing the translated image of the object onto the sensor array by adjusting the distance separating the sensor array and the proximal end of the lens means and for maintaining the longitudinal axis of the lens means. Thumb wheel 208 engages interlocking ridges 210 disposed on the exterior surface of optical coupler 90, sliding optical coupler 90 along proximal portion 108 of lens tube 32, thus allowing one to position the CCD array, thereby focusing the camera. Thumb wheel 208 also assists in preventing lens-fiber module 88 from moving in a lateral direction toward the sides of first housing 202, thus maintaining the longitudinal axis of the lens means. Mechanical stop 211 is provided proximal to CCD array circuit board 80 to prevent optical coupler 90 from sliding off the proximal portion 108 of lens tube 32.

It will be appreciated that portable endoscopic camera 200 may be adapted with a variety of features discussed previously with regard to portable endoscopic camera 10. For example, a variety of light source means, as discussed previously are also available for use in camera 200, including external bulbs, bulbs within an external enclosure, and bulbs coupled through a cable, such as a fiber optic cable, to the lens means. Also by way of example, in one embodiment, a power supply means such as battery pack 35 demonstrated in FIG. 1, is mounted on first housing 202. In another embodiment, disposable batteries or a rechargeable acid lead cell are disposed within first housing 202. A variety of other power supply means are also available, including cord-operated power.

Similarly, various display means are electrically coupled to the camera assembly 67 within first housing 202. For example, in one embodiment, the display means is a monitor, such as monitor 36 of FIG. 1, mounted on first housing 202. Cord-operated composite video output capability, S-VHS output capability, may also be provided within first housing 202, as well as transmitter means.

Thus, first housing 202 is another example of hand-held means for housing the light source means, video imaging means, lens means, and power supply means, such that the apparatus is self-contained and convenient to manipulate. As shown in FIG. 9, single chambered first housing 202 includes a housing body 204 and a corresponding lid 206, the interior surfaces of housing body 204 and lid 206 defining a single chamber.

In yet another embodiment, self-contained camera 200 is comprised of first housing 202, second housing 201, the components within first housing 202, the components within second housing 201, and means for electrically coupling the components of the first and second housings 202–201 such as a cable, shown in FIG. 8 extending from outlet port 203.

Second housing 201 is conveniently held in a practitioner's hand or mounted on the practitioner's belt, for example. It will also be appreciated that in yet another embodiment, the components of camera 10 of FIG. 1 are electrically coupled to the contents of second housing 201. In one embodiment, second housing 201 contains a power supply means electrically coupled to, and for supplying electrical power to the light source means, video imaging means, transmitter means, and/or display means. Second housing 201 (or second housing 608 shown in FIG. 30) may also conveniently house a transmitter means, display means and/or light source means (such as a halogen bulb in the range of about 50 to about 100 watts, for example) connected through a cable to the lens means. Outlet port 205 is typically employed for connection to optional cord-operated power supply means, or separate display means, such as a wall or desk mounted monitor.

3. Third Housing Embodiment

FIG. 10 demonstrates another embodiment of a portable endoscopic camera 220. Camera 220 is similar to camera 200. As shown in the embodiment of FIG. 10, however, the longitudinal portion 222 (shown in FIG. 4) of input port 110 parallel lens tube 32 is removed and lens fiber bundle 112 terminates in the angled portion 224 of input port 226 which is at an angle with respect to the longitudinal axis of lens tube 32. Thus, fiber bundle 112 terminates immediately after entering fiber light input port 226 at an angle from lens tube 32. Bulb 100 of lamp assembly 94 abuts the fiber bundle 112 directly after fiber bundle 112 exits lens tube 32 in this angled position, bringing bulb 100 closer to lens tube 32 and avoiding the travel of light through longitudinal portion 222. FIG. 11 is an example of portable endoscopic camera 220 of FIG. 10 adjusted by thumbwheel 208 such that optical coupler 90 is directed proximally along the longitudinal axis of lens tube 32.

4. Fourth Housing Embodiment

Figure 16:
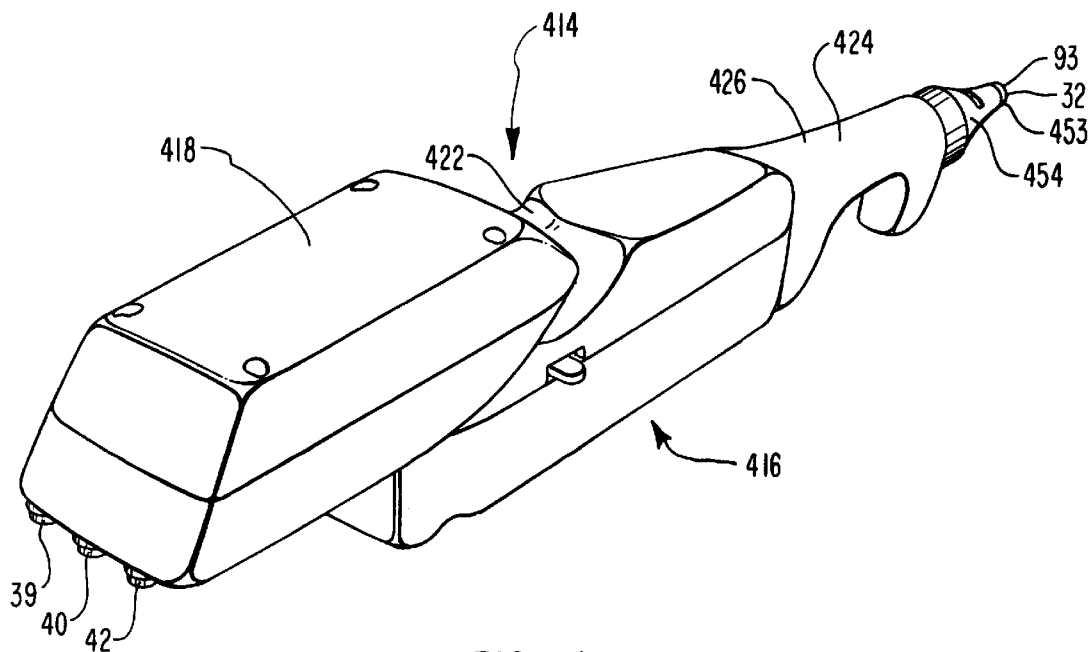
FIG. 16 is a perspective view of another embodiment of a portable endoscopic camera.

The self-contained portable endoscopic camera 414 of FIG. 16 features yet another example of a first housing means. As shown in FIGS. 16 and 17, first housing 416 includes a top lid 418, a bottom lid 420, a housing body 422, and a stabilizing means for stabilizing camera 414. In one embodiment, the stabilizing means comprises distal grip 424, which is designed for placement of the practitioner's thumb or fingers thereon during use. Distal grip 424 acts as a safety means, stabilizing camera 414, such as when lens tube 32 (and/or a coupled probe means) is disposed within a sensitive bodily orifice, such as an ear.

By holding the grip 424 with a thumb, finger or fingers, and by placing one or more fingers near the object to be illuminated, the practitioner is able to stabilize camera 414 while holding the distal end 93 of the lens tube 32 closely adjacent an object. For example, if the practitioner is viewing inside a patient's ear, the practitioner can hold grip 424 and simultaneously place one or more fingers on the side of a patient's head, thereby further stabilizing camera 414 and precisely orienting distal end 93.

Grip 424 comprises a contoured housing 426 with a cylindrical channel (not shown) extending therethrough for reception of the lens tube 32. Also as shown in FIG. 16, the distal end 93 of the lens tube 32 extends through the grip 424 and distally from the distal end 453 of probe adapter 454, such that the distal end 93 of the lens tube protrudes slightly through probe adapter 454. The slight protrusion of distal end 93 distally from the distal end 453 of probe adapter 454 provides a clear resolution by camera 414. In one embodiment, the distal end 93 of the lens extends approximately 1/32 of an inch distally from the distal end 453 of probe adapter 454.

The battery pack 35 of FIG. 1 is not shown as included on camera 414 in FIG. 16. Employing a second housing means, such as second housing 201, for example, may be advantageous because of the weight associated with battery pack 35. A lighter weight device is more readily stabilized by the practitioner. However, in another embodiment, the battery pack 35 shown in FIG. 1 is mounted on top lid 418 of first housing 416.

Thus, first housing 416 is another example of hand-held means for housing the light source means, video imaging means, lens means, and power supply means, such that the apparatus is self-contained and convenient to manipulate. It will be appreciated that portable endoscopic camera 414 may be adapted with a variety of features discussed previously with regard to portable endoscopic camera 10.

In one embodiment, the components of the top cavity (not shown) of camera 414 are the same or substantially similar to that of top cavity 52 camera 10 of FIG. 1. To prevent transmitter interference, a rectangular copper ground plate is preferably provided above the transmitter in a compartment of top lid 418. A lead from the ground plate is soldered to the transmitter board. In a preferred embodiment, the transmitter is an FM transmitter for sending signals to an FM receiver.

With reference now to FIG. 17, in a preferred embodiment, the bottom lid 420 of camera 414 includes an interior surface designed for reception of the lens fiber module 88 and to accommodate the sleeved lamp assembly 94 as well as the back and forth movement of CCD board 80.

To avoid the use of lubrication for moving parts, in each of the housing embodiments disclosed herein, a highly polished type of housing 202 may be used. Each of the housings may be water proof or water resistant, such as by providing a sealed housing and disposing a rubber grommet or O-ring around the seals. In addition, water tight electrical adapters may be employed in conditions where water damage is likely, such as surgery or underwater procedures. In these procedures, a rubber or plastic seal is placed about the adapters and/or probes. Focus wheel 208 or focus bridge 92 of FIGS. 3 and 9 are removed and the housing surrounding them, such as slots 26 may be filled in for increased water tight or water proof capability. During operation, a set screw may be employed on the external surface of the housing to set the focus, the set screw communicating with a corresponding sprocket within the housing, the sprocket interlocking with tracks 210 on optical coupler 90 for sliding coupler 90.

5. Fifth Housing Embodiment

A cross-sectional side view of another housing embodiment of self-contained camera 510 is shown in FIG. 27. As shown in this embodiment, first housing 574 comprises a single chambered housing 574 in which bulb 100, is disposed against proximal fiber bundle 540. Sleeve 575 made from translucent elastomer (e.g., colorless and high gloss), such as nylon, or another suitable material, surrounds light bulb 100 and couples bulb 100 to collar 544.

Wireless video transfer may be achieved through the use of a transmitter 70 disposed in transmitter housing 572. It will be appreciated that it is possible to dispose power supply means within or on first housing 574. For example, battery pack 35 of FIG. 1 may readily be placed on first housing 574. Also as shown in FIG. 27, in one embodiment, ribbon cable 78 of the video imaging means is in a fixed position with respect to the CCD board 80, thereby preventing breakage or displacement of the ribbon 78 from CCD board 80 or the video imaging means.

As shown in FIG. 27, camera 510 further comprises means for replacing the light source means, including set screw 640, which serves as a door for replacing the light source means. Spring 642 presses against bulb, assisting in retaining bulb in an abutting relationship with fiber bundle and thereby serving as another example of means for retaining the light source means in an abutting relationship with the lens means. A negative plate 644 and a positive plate 646 of the power supply means may be disposed within sleeve 575, the negative plate 644 contacting socket 513 and positive plate 646 contacting spring 642, which contacts socket 513, thereby supplying electrical power to bulb 100.

Figure 30:
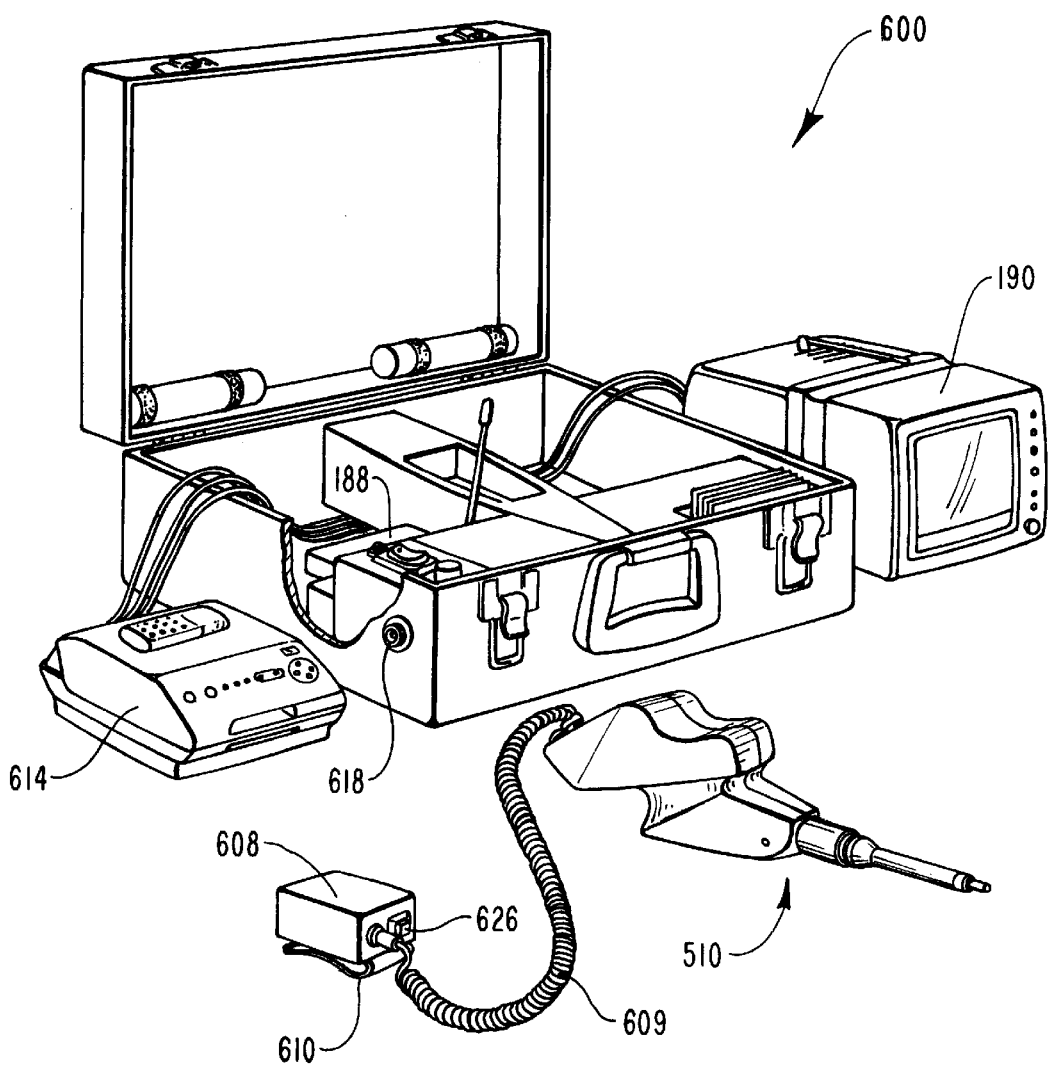
FIG. 30 is an exploded view of the kit of FIG. 29.

In addition, it will be appreciated that a variety of components discussed above in any of the foregoing camera embodiments may be employed in camera, such as voltage regulator 68. As shown in FIG. 30, in one embodiment, self-contained camera 510 is comprised of first housing 574, second housing 608, the components within first housing 574, the components within second housing 608, and means for electrically coupling the components of the first and second housings 574–608 such as a cable 609.

L. Adapter Means

The invention further comprises a variety of adapter means for optically coupling probe means to the distal end of the lens means. Probe adapter 30 is one example of an adapter means, as discussed above and shown in FIGS. 1–3.

Figure 23:
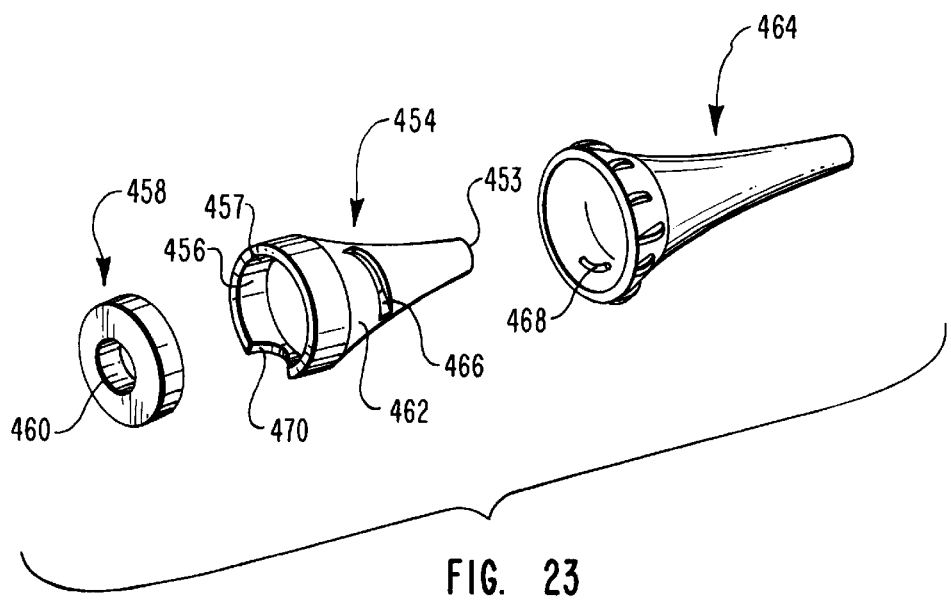
FIG. 23 is an exploded view of a washer, probe adapter, and probe of the portable endoscopic camera of FIG. 16.

Another example of an adapter means is adapter 454, shown in FIG. 23. As shown, adapter 454 is comprised of a neck 456 having an interior surface 457 defining a passageway. In one embodiment, the passageway is configured for the placement of lens tube 32 therein. In another embodiment, the passageway is configured for the placement of washer 458 therein, as shown in FIG. 17. Inside surface 460 of washer 458 is configured to be press fit about distal end 93 of lens tube 32. Washer 458 thus couples lens tube 32 to probe adapter 454.

An adapter body 462 integrally attached to adapter neck 456 extends inwardly and distally from adapter neck 456. In one embodiment, adapter body 462 has a hollow conical shape, as shown in FIG. 23. In a preferred embodiment, the exterior surface of adapter body 462 is designed to mate with the interior surface of a probe, such as the otoscope speculum 464 shown in FIG. 23. To secure a probe such as speculum 464 to probe adapter 454, adapter body 462 includes a groove 466 for reception of a ridge 468 on the interior surface of the probe.

In order to rotate adapter 454 about lens tube 32, adapter 454 further includes aligning means for aligning adapter 454 with respect to lens tube 32. Recess 470 and washer 458 are an example of aligning means. A practitioner desiring to properly orient a probe, in order place the probe within a patient's eye socket, for example, may press against the recessed portion 470, thereby rotating adapter 458 with respect to lens tube 32 until the probe is properly aligned. As opposed to be threads, washer 458 may be rotated many times without unscrewing from distal end 32. This aligning feature of probe recess 470 will be discussed in additional detail below with reference to FIGS. 24 and 25. It will be appreciated that as an alternative to employing a washer, the aligning function could be achieved by the adapter 454 having a smooth interior surface such as surface 460 which is adapted to be disposed about lens tube 32.

Preferably, the probe adapter 454 is designed to couple a variety of different probes to lens tube 32. Probe adapter 454 may also be adapted to a variety of different washers having different inner diameters which can be used to mount adapter 454 on different lens tubes.

Figure 28:
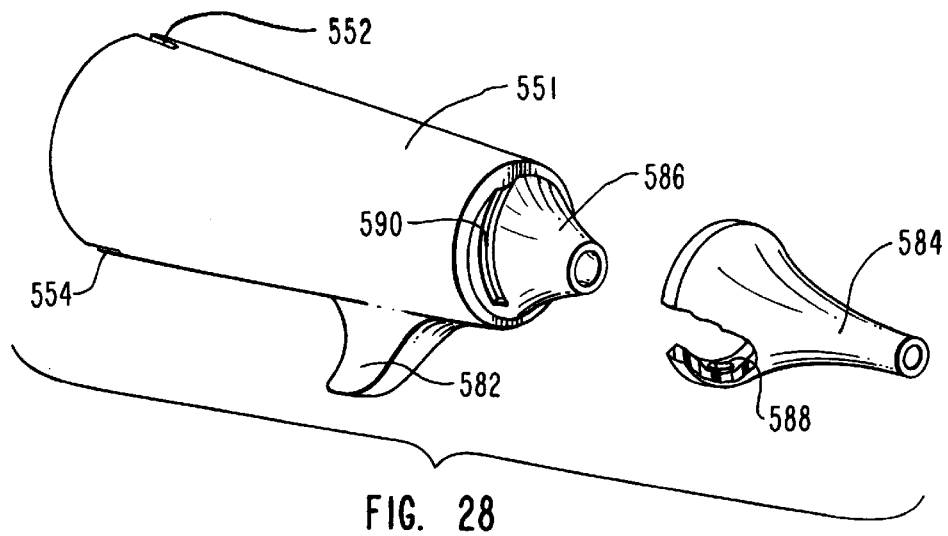
FIG. 28 is an exploded view of an adapter designed for placement on the distal end of the camera of FIG. 26 and a probe placed on the adapter.

As shown in FIG. 28, in another embodiment, an adapter 551 includes a handle 582 for placement of the fingers during use of apparatus 510. A variety of probes, such as probe 584 may be coupled onto the distal portion 586 of adapter 551. In one embodiment, to couple a probe to the adapter, an insert 588 within probe 584 is inserted within a slot 590 in adapter 551. In a preferred embodiment, slot 590 is shallow, such that insert 588 compresses against the inside surface of slot 590, thereby forming a tight fit, maintaining the insert 588 tightly within slot 590. Adapter 551 is preferably autoclavable.

In another embodiment, an insert 550 on the lens fiber module 512 mates with a first or second peripheral slot 552, 554 on adapter 551, shown in FIG. 28, thereby maintaining adapter 551 securely on housing 518. Also as shown in FIG. 27, in one embodiment, an O-ring 548 is disposed about housing 518 to seal the securement between the exterior surface of housing 518 and adapter 551. The first and second slots of adapter 551, each of which are contiguous with at least one groove on the interior surface of adapter 551, allow adapter 551 to be twisted and locked in place on insert 550.

Because of the use of first and second slots, disposed approximately 180 degrees apart, as opposed to merely one slot, either slot of adapter 551 may be mounted on insert 550. Thus, a probe such as mirror speculum 292 discussed below may be coupled to adapter 551 with mirror 300 facing upwardly or downwardly, depending on the orientation of adapter 551, without twisting apparatus 510 upside down. Mirror speculum 292, can thus be used to view upper or lower molars without twisting camera 510 upside down. Instead, to change views, the slot of adapter 551 though which insert 550 is disposed is merely alternated, thereby switching the position of mirror 300. Slots 552, 554 serve as additional examples of aligning means for aligning adapters 551 with respect to the lens tube.

M. The Interchangeable Probes

Figure 12:
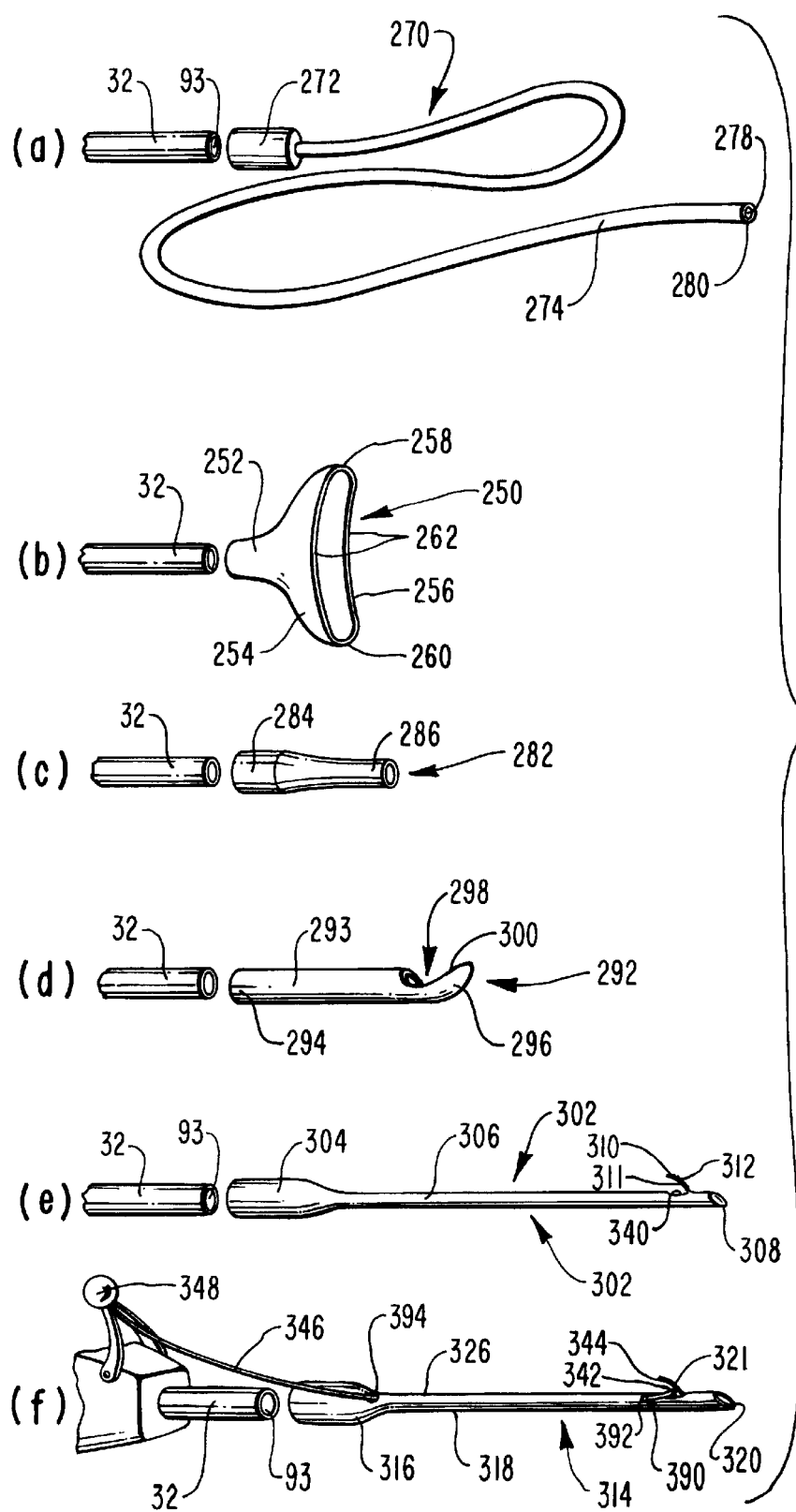
FIG. 12a through 12h are perspective views of a variety of probes which may be placed directly on the lens tube of the various embodiments of portable endoscopic cameras disclosed herein or may be coupled to the lens tube by adapter means.

As a further aspect of the present invention, portable endoscopic camera in each embodiment herein disclosed is highly versatile in that a variety of probe means may be optically coupled to the lens means, either directly to the distal end of the lens tube 32 or through an adapter means disposed on lens tube 32, such as discussed above. In one embodiment, the probe means disclosed in FIG. 12 are specifically designed to fit directly on lens tube 32. In this embodiment, lens tube 32 has a universal design which mates with a variety of probes. When a different probe is needed, a new adapter or camera is not required. In another embodiment, a probe adapter, such as adapter 454 or adapter 551 is disposed between the lens tube 32 and the probe, the adapter having a design universal to a variety of probes.

Probes may be secured to lens tube 32 or an adapter in a variety of ways. In one embodiment the lens tube 32 has external threads which mates with internal threads within the necks of the probes. In another embodiment, a single ridge on the probe mates with a single groove on lens tube 32 or a single groove on the probe mates with a single ridge on lens tube 32. The probes may be made from stainless steel, plastic, aluminum or a variety of other materials known by those skilled in the art.

In one embodiment, each of the probes employed in combination with the endoscope embodiments described herein includes reflecting means for reflecting light in a desired direction. For example, in one embodiment, the reflecting means is comprised of a reflective material, such as a white or light gray plastic material on the interior and exterior surfaces of the probe. It is believed that the light color fosters reflection of the light onto the object, whereas a black material absorbs the light.

FIG. 12a demonstrates a fiber optic cable probe 270 for use in inspecting a variety of objects. Fiber optic cable probe 270 is designed for wrapping around a wall, for example, to view objects on the other side or for disposition into structures such as computer equipment, anatomical orifices, or in a variety of other places.

Fiber optic cable probe 270 is comprised of a neck 272 having an interior surface defining a passageway for placement of lens tube 32 or an adapter therein. A fiber optic cable 274 extends distally from neck 272, a proximal end of fiber optic cable 274 preferably disposed against the distal end 93 of lens tube 32. A distal lens 278 is disposed at the distal end 280 of fiber optic cable 274. Thus, an image illuminated by fiber optic cable 274 and viewed through distal lens 278 is translated through fiber optic cable 276 to lens tube 32. While fiber optic cable 274 may be designed to have varying lengths, it is preferably designed to be approximately three feet long, to reach around various objects.

FIG. 12b demonstrates one embodiment of an eye speculum 250 for use in inspecting a variety of objects, such as the eye and related anatomy. For example, eye speculum 250 may be employed in photographing stages of cataract maturation and for use in plastic surgery relating to the eyelids. Eye speculum 250 is contoured similar to an eye wash cup for rinsing the eye.

Eye speculum 250 is comprised of a neck 252 having an interior surface defining a passageway for placement of lens tube 32 or an adapter therein. A speculum body 254 integrally attached to speculum neck 252 extends outwardly and distally from neck 252. Speculum body 254 is contoured at a distal end 256 in an approximate oval shape, having a rounded first side edge 258, a rounded second side edge 260 and opposing upper and lower edges 262 which recess proximally with respect to first side edge 258 and second side edge 260 such that the speculum 250 is placed within the eye socket for inspection of the eye when coupled to lens tube 32. The distance between first side edge 258 and second edge 260 is greater than the distance between opposing upper and lower edges 262.

Figure 25:
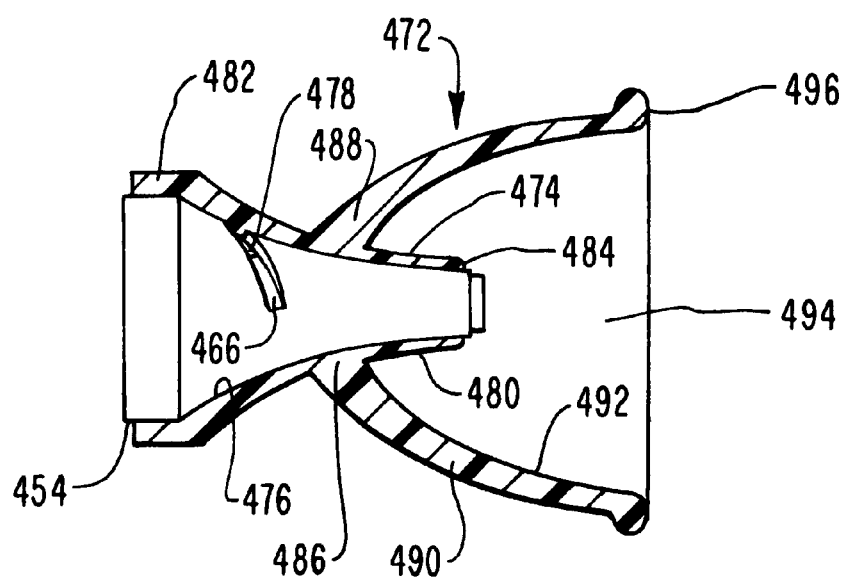
FIG. 25 is a cross sectional view of the optical probe of FIG. 24 assembled on the probe adapter of FIG. 23.

FIGS. 24 and 25 demonstrate another embodiment of an eye speculum 472 for use in inspecting a variety of objects, such as the eye and related anatomy. For example, eye speculum 472 may be used in photographing stages of cataract maturation and in plastic surgery relating to eyelids.

Eye speculum 472 is comprised of a neck 474 having an interior surface 476 defining a passageway for placement of lens tube 32 or, as shown in FIG. 25, probe adapter 454 therein. Also as shown in FIG. 25, an internal ridge 478 on the interior surface 476 of speculum fits within groove 466 on probe adapter 454, maintaining probe adapter 454 and speculum 472 in a secure relationship.

Neck 474 further comprises an exterior surface 480 having a proximal end 482, a distal end 484, and an intermediate portion 486. A body 488 configured to fit about the eye socket extends outwardly and distally from intermediate portion 486 of exterior surface 480 of neck 474. Body 488 has an exterior surface 490 and an interior surface 492 defining a distal speculum cavity 494.

Body 488 is contoured at a distal end 496 thereof in an approximate oval shape having a rounded first side edge 498, a rounded second side edge 500 and opposing upper and lower edges 502 which recess proximally with respect to first side edge 498 and second side edge 500 such that speculum 472 is placed within the eye socket for inspection of the eye when coupled to lens tube 32. The distance between first side edge 498 and second side edge 500 is greater than the distance between opposing upper and lower edges 502.

As shown in FIG. 25, a distal portion 484 of neck 474 extends into the cavity 494 defined by the interior surface 492 of body 488, thereby positioning distal end 93 of lens tube 32 at a predetermined distance from the eye. By extending past the interior surface 492 of body 488, the neck 474 allows lens tube 32 to be positioned close to the eye, a significant advantage within the art. In addition, it is possible to position neck 474 such that distal end 93 of lens tube 32 protrudes slightly distally from the distal end 484 of probe adapter 454, providing a clearer resolution, as discussed above.

As will be appreciated, recess 470 of probe adapter 454 allows the practitioner to rotate speculum 472 such that speculum 472 fits into the eye socket without rotating the endoscopic camera housing 416. Thus, if speculum 472 is not initially aligned with the eye socket, the practitioner can rotate probe adapter 454 until speculum 472 is aligned, rather than rotating housing 416 and maintaining housing 416 in an awkward position in order to align speculum 472 with the eye socket.

FIG. 12c demonstrates an otoscope speculum 282 for use in inspecting a variety of objects. Otoscope speculum 282 is comprised of a neck 284 having an interior surface defining a passageway for placement of lens tube 32 or an adapter therein. A speculum body 286 integrally attached to speculum neck 266 extends inwardly and distally from neck 284.

In another embodiment of otoscope speculum 282, it is possible to flush an ear or other cavity while looking into the cavity, employing a means for flushing, the flushing means attached to housing 12, lens tube 32 or otoscope 282. Such flushing means includes, for example, a tube which is parallel lens tube 32 and the longitudinal axis of otoscope speculum 282. A syringe disposed at a proximal end of the tube releases flushing fluid into the tube. The tube has an opening at a distal end near the distal end of otoscope 282 for the release of fluid into the cavity during the observation.

In yet another embodiment of otoscope speculum 282, speculum 282 is made from a light reflective material, such as a light gray plastic material, thereby reflecting the light produced by the light source means onto an object.

Figure 12G:
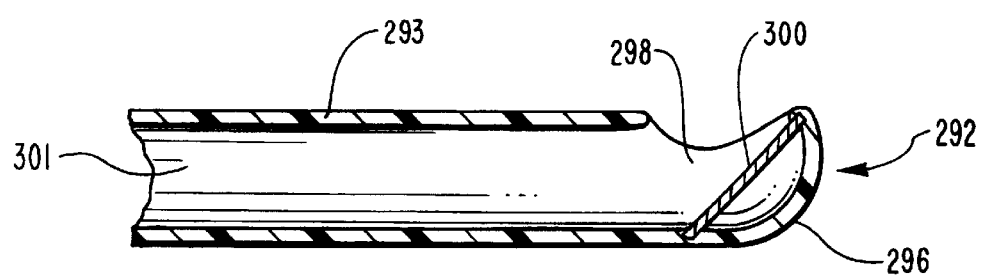

FIGS. 12d and 12g demonstrate in a perspective view and in cross section, respectively, a mirror speculum 292 for use in inspecting a variety of objects, such as a tooth. For example, mirror speculum 292 can be employed to inspect cracks in teeth or gum disease. Mirror speculum 292 is comprised of a tubular housing 293 having an interior surface 301 defining a passageway. Tubular housing 293 is configured for placement of lens tube 32 or an adapter therein. A distal end 296 is closed. Tubular housing 293 includes an aperture 298 proximal to distal end 296. Aperture 298 is configured for reception of an object such as a tooth. A mirror 300 is disposed in the passageway within housing 293 adjacent aperture 298 and is oriented to reflect the image of the received object into lens tube 32. Preferably, lens tube 32 is disposed within housing 293 such that distal end 93 of lens tube 32 is approximately ½ inch from mirror 300.

FIG. 12e demonstrates a first biopsy speculum 302 for use in inspecting a variety of objects and for taking a biopsy of an inspected object without making an incision. First biopsy speculum 302 is comprised of a neck 304 having an interior surface defining a passageway for placement of lens tube 32 or an adapter therein. A speculum body 306 integrally attached to speculum neck 304 extends inwardly and distally from neck 304. Speculum body 306 is in the shape of a needle and contains a fiber optic cable, preferably a single fiber optic strand. A proximal portion of the fiber optic cable is preferably disposed against the distal end 93 of lens tube 32. The fiber optic cable includes a lens at distal end 308 for viewing the area to be biopsied.

A spoon 310 having a serrated distal face 312 is disposed near distal tip 308 for taking a biopsy sample while biopsy speculum body 306 is disposed within the area to be biopsied. Thus it is possible for the practitioner to view the area, through lens tube 32 and take a biopsy with spoon 310.

As spoon 310 scrapes biopsied material, the material accumulates in groove 340. At least one side 311 of spoon 310 is sharpened such that upon twisting speculum 302 the sharpened side 311 makes an incision. Spoon 310 is then employed to scrape and retrieve the incised portion.

FIG. 12f demonstrates a second biopsy speculum 314 for use in inspecting a variety of objects and for taking a biopsy of an inspected object without making an incision. Second biopsy speculum 314 is comprised of a neck 316 having an interior surface defining a passageway for placement of lens tube 32 or an adapter therein. A speculum body 318 integrally attached to speculum neck 316 extends inwardly and distally from neck 316. Speculum body 318 is in the shape of a needle and contains a fiber optic cable, preferably a single fiber optic strand. A proximal portion of the fiber optic cable is preferably disposed against the distal end 93 of lens tube 32. The fiber optic cable includes a lens at distal end 320 for viewing the area to be biopsied.

A spoon 321, possibly having a serrated distal end 320, is pivotally mounted on a pivot pin, for example, within speculum body 318 near distal end 320, for taking a biopsy sample while biopsy speculum body 318 is disposed within the area to be biopsied. Thus it is possible for the practitioner to view the area, through lens tube 32 and take a biopsy with spoon 310.

As spoon 321 scrapes biopsied material, the material accumulates in groove 342. At least one side 344 of spoon 321 is sharpened such that upon twisting speculum 314 the sharpened side 344 makes an incision. Spoon 321 is then employed to scrape and retrieve the incised portion.

Second biopsy speculum body 318 further comprises a tube 390 disposed parallel to the fiber optic cable for disposition of a wire 346 therethrough. Wire 346 or other means for directing spoon 321 is disposed within tube 390. Wire 346 exits a distal end 392 of the tube 390 and at a distal end of wire 346 attaches to spoon 321 for pivoting spoon 321 in a proximal or distal direction. Spoon 321 is preferably pushed distally against body 318 as speculum 314 is disposed into the body or other cavity, minimizing the interference of spoon 321 against the skin. Wire 346 exits a proximal end 394 of tube 390 and is attached at a proximal end of wire 346 to a lever 348 mounted on neck 316, lens tube 32, or on a distal portion of the camera housing. Wire 346 assists in orienting spoon 321 in a desired position.

Figure 12H:
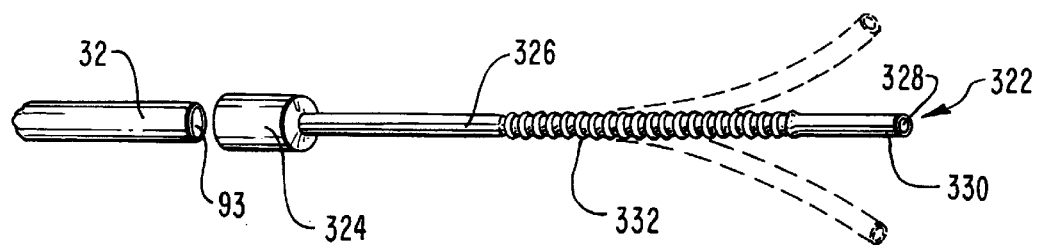

FIG. 12h demonstrates a memory probe 322. Memory probe 322 is selectively shaped and retains its selective shape for use in inspecting a variety of objects. Memory probe 322 is designed for bending into a particular shape and for retaining the shape. Thus, the probe 322 can be wrapped around a wall or other structure and used in its originally selected shape.

Memory probe 322 is comprised of a neck 324 having an interior surface defining a passageway for placement of lens tube 32 or an adapter therein. A fiber optic cable 326 extends distally from neck 324, a proximal end of fiber optic cable 326 preferably disposed against the distal end 93 of lens tube 32. A distal lens 328 is disposed at the distal end 330 of memory probe 322. Thus, an image illuminated by memory probe 322 and viewed through distal lens 328 is translated through fiber optic cable 326 into lens tube 32. Fiber optic cable 326 is preferably approximately one foot in length.

In order to create the memory dynamic, a memory plastic having accordion-shaped ribs 332, such as used with memory plastic flexible drinking straws, coats the outer surface of fiber optic cable 326. Preferably a non-ABS plastic is employed.

FIG. 13 demonstrates a coupler 352, which is an example of a means for coupling the lens means to a funnel-shaped probe 350. Funnel shaped probes are particularly useful for the inspection of the ear. Coupler 352 includes a neck 364 having an interior surface defining a passageway for placement of lens tube 32 or an adapter therein. A coupler body 356 integrally attached to neck 364 extends outwardly and distally from neck 354 in a funnel shape. Coupler body 356 is contoured at a distal end 358 in a circular shape. A clamp, such as a circular-shaped clamp or a C-shaped "C" clamp 360 made of flexible plastic or rubber extends from the distal end 358 of coupler body 356 and is disposed about funnel probe 350 for retaining the distal end 358 of coupler 352 in an abutting relationship with the proximal end 359 of funnel probe 350. In one embodiment, distal end 93 of lens tube 32 is disposed against the proximal end of a fiber optic cable disposed within funnel-shaped probe 350 in an abutting relationship.

FIGS. 14 and 15 demonstrate microscope coupler 361. Microscope coupler 361 is an example of a means coupled to a microscope 362 for translating an image within the microscope 362 into the lens means of portable endoscopic camera 10. Microscope coupler 361 includes a neck 364 having an interior surface defining a passageway for placement of lens tube 32 or an adapter therein. A coupler body 366 integrally attached to neck 354 extends outwardly and distally from neck 364. Coupler body 368 includes dual ring shaped ports 370 configured to receive the microscopic eye-pieces 372. A C-clamp 378 is used, for example, to retain eye-pieces 372 within ports 370.

As shown in cross section in FIG. 15, the image viewed within each microscopic eye-piece 372 is projected to a corresponding side mirror 374 within microscope coupler 361. Each side mirror 374 reflects the image onto a central mirror 376, which reflects the combined image to lens tube 32.

The advantage provided by microscope coupler 361 is that it allows a practitioner to add additional magnification to a microscoped image. In addition, the practitioner is able to transmit the image through signal unit 70, for example, to a wall mounted monitor for viewing of the image by a larger number of practitioners.

In addition to the variety of possible uses of the disclosed endoscopic camera, various modifications increase the potential uses for the invention. For example, it is possible to remove lens fiber module 88 and place the apparatus in a remote control activated device, such as model air plane or model car. A full size lens is mounted on the camera, for example. A monitor, such as a liquid display monitor, is then mounted on a remote control operating device. Thus, the operator could view the flight path of the airplane, for example in the display monitor. In another embodiment it is possible to remove lens fiber module 88 and employ the remaining hand held unit to see around corners or within or through walls, for example. In another embodiment, it is possible to employ the battery operated device as a security camera, with or without lens fiber module 88.

N. The Portable Kit

Figure 29:
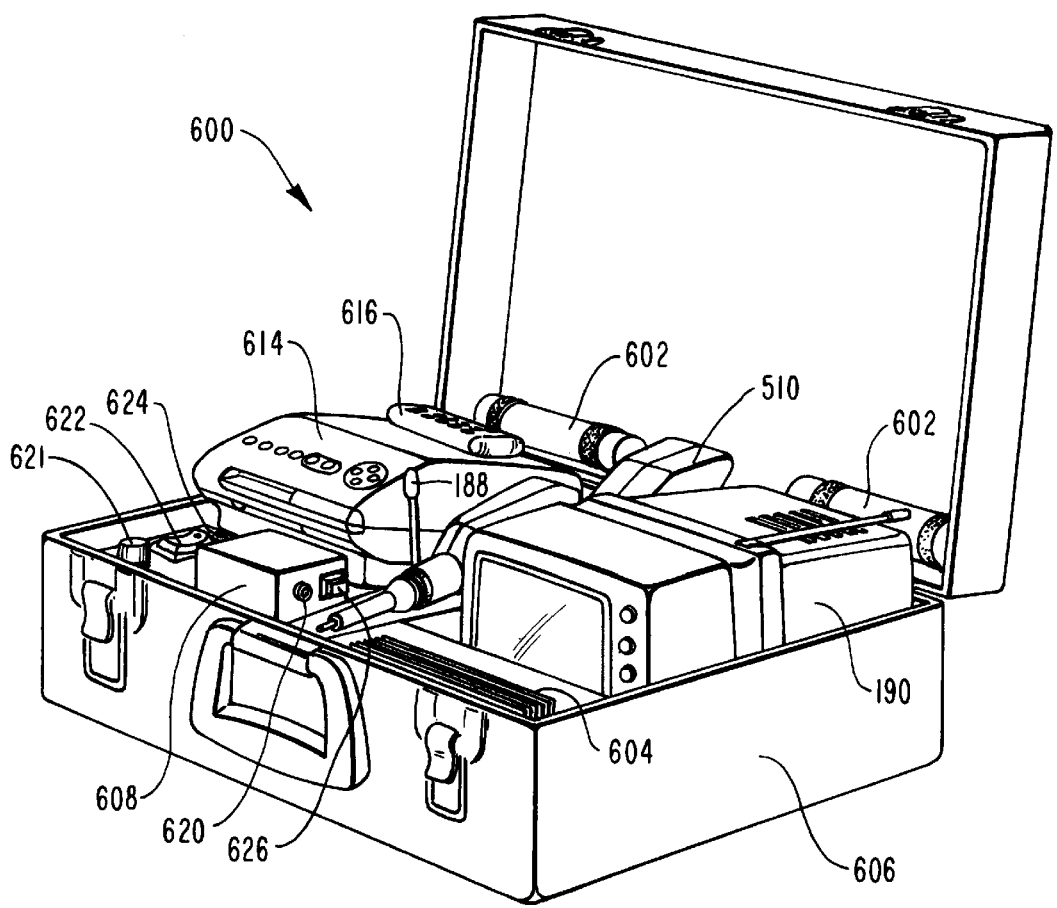
FIG. 29 is a perspective view of a kit for producing video images of an object.

With reference now to FIGS. 29 and 30, the present invention also includes a kit 600 for producing video images of an object. In one embodiment, kit 600 comprises (i) the portable, hand-held apparatus for producing video images of an object described in any of the foregoing embodiments, such as camera 510, camera 510 including second housing 608; (ii) display means for displaying video images of the object, including for example, a monitor 190 and/or a printer 614; (iii) accessory containers 602 for containing probes, couplers, adapters and other accessories; (iv) a receiver 188 for receiving video signals transmitted by the transmitter means; (v) a variety of different supplies, such as paper 604 for printer 614 or other miscellaneous supplies; (vi) a portable container 606 for portably containing a variety of components of the invention; (vii) a remote control unit 616 for controlling monitor 190 and/or printer 614; and (viii) power supply means disposed within the container 606 for supplying electrical power to the display means, such as monitor 190 and printer 614, and the receiver means.

Kit 600 is uniquely well suited for traveling to a remote location in which electricity is not readily available, and in which the practitioner is required to move freely with respect to container 606. By employing kit 600, a practitioner may from a location remote from container 606 and make a video image of an object, such as a patients' ear, which is sent to monitor 190 within container 606. For example, a first practitioner may perform an endoscopic examination in a room remote from another room in a clinic or the practitioner's automobile in which the container 606 has been placed. While the first practitioner performs the examination, a second practitioner may view monitor 190 from the separate room or automobile. Even if container 606 is in the same room with the first practitioner, the practitioner is not required to drag annoying cables around the room to view images on monitor 190.

Accessory containers 602, such as cylinders 602 may be attached by hook and pile, such as VELCRO, to container 606, the cylinders 602 containing probes, couplers, or other accessories to be employed in conjunction with kit 600.

In addition, kit 600 includes second housing 608 of camera 510 which, in one embodiment, contains a rechargeable battery pack to provide electrical power to the components within or otherwise attached to first housing 574, through the use of a means for coupling the components of the first and second housings 574, 608, such as a cable 609. As shown, a clip 610 is provided for mounting the second housing 608 to the individual's belt, for example. Belt mounted second housing 608 also includes an on/off button 626 and a jack 620 for coupling the components of first housing 574 to the components of second housing 608. Through the use of at least one battery disposed within second housing 608, camera 510 may be operated as a self-contained unit.

As shown in FIG. 30, receiver 188 is coupled to monitor 190 and/or printer 614. By employing transmitter 70 and receiver 188, wireless video transfer may occur between endoscopic camera 510 and the components of container 606, such as monitor 190. Container 606 also includes an integral power supply means, such as a battery (not shown) coupled to receiver 188, monitor 190 and printer 614 for supplying electrical power to receiver 188, monitor 190 and printer 614. Upon actuating an on/off switch 622 coupled to fuse 621, a light emitting diode 624 indicates that the power has been turned on. In one embodiment, the integral battery is disposed within a compartment within container 606 beneath on/off switch 622. The battery is preferably rechargeable through jack 618. It is also possible to power camera 510 by providing camera 510 with power from the battery in container 606, such as by plugging cable 609 into jack 618 of container 606. Container 606 thus serves as another example of a second housing means.

Figure 31:
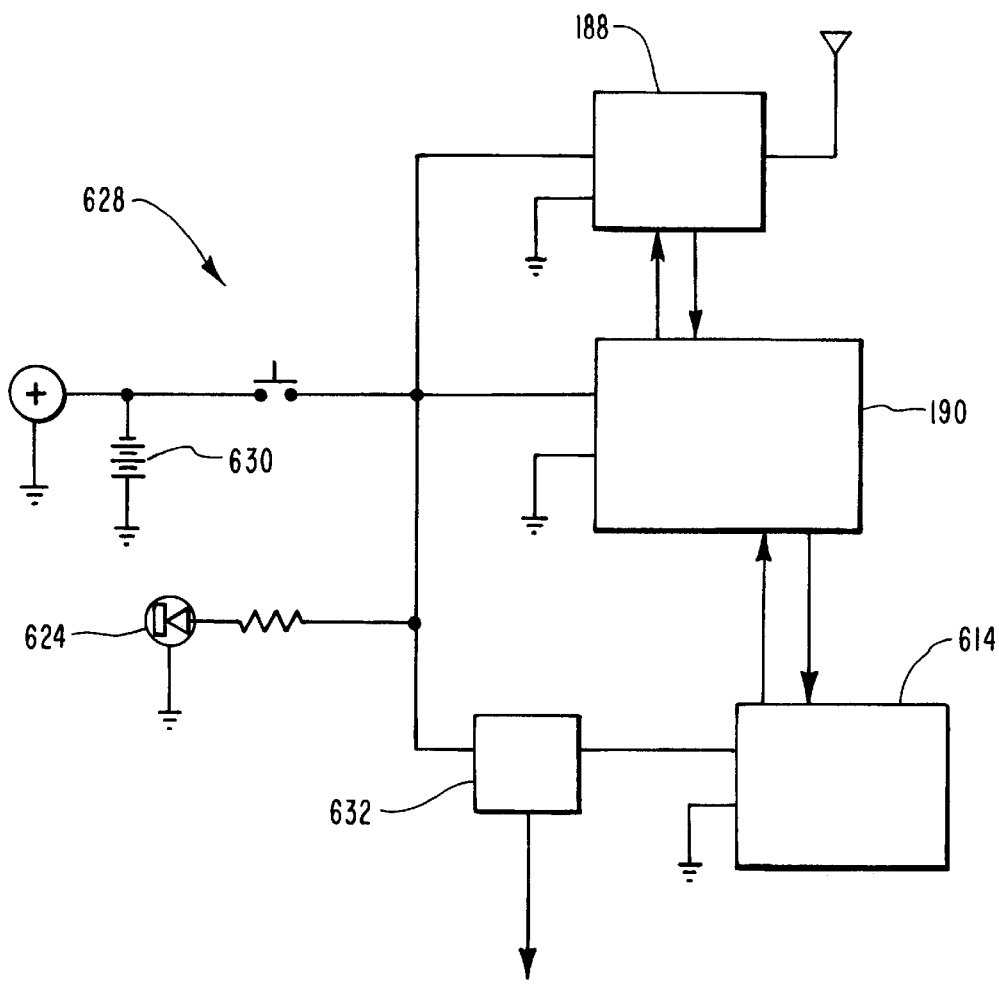
FIG. 31 is a wiring diagram of the kit of FIG. 29.

With reference now to FIGS. 30 and 31, to conserve space, in one embodiment, the power supply means disposed within the container 606 comprises a battery having an output of approximately 12 volts of electrical power. While 12 volts may be suitable for a typical portable monitor, typically, portable printers, such as printer 614 require more voltage than portable monitors. Thus, in a preferred embodiment, kit 600 further comprises means for converting the voltage of the power supply means to a voltage sufficient to provide electrical power to the printer. For example, in one instance, the converting means comprises a power converter 632, which converts approximately 12 volts of electrical power to the approximately 22 volts of electrical power required to power printer 614. Thus, it is possible for a practitioner to power both the monitor and the printer by using a single 12 volt battery as opposed to employing two 12 volt batteries or a single 24 volt battery. Otherwise, a battery of significantly greater size or the use of multiple 12 volt batteries would be required to be used within container 606, which would be inconvenient, heavy, and cumbersome to locate within container 606.

With continued reference to FIG. 31, an example of a wiring diagram 628 for portable container 606 is shown. In one embodiment, a twelve volt battery 630 is employed to power a wireless receiver 188, a monitor 190 coupled to receiver 188, and a printer 614 coupled to the monitor 190, and an "on" indicator 624, such as a light emitting diode. Also as shown, in one embodiment, power converter 632 converts the approximately twelve volt current to the approximately twenty two volts required by printer 614.

To illustrate the advantages of the hand-held apparatus and kit, suppose, for example that a medical practitioner desired to visit a series of clinics in a remote area having no electricity. While riding in a vehicle in between clinics, a practitioner can recharge container 606 and/or apparatus 510 from the cigarette lighter port of the vehicle. Even though the clinic lacks electricity, upon reaching the clinic the practitioner can perform an endoscopic examination, view the results within the monitor, and print a copy of the results. Because of the wireless video transfer capability, it is possible for the practitioner to perform the examination without dragging cables around the patient examined. It is even possible to leave the container 606 in the vehicle for another practitioner to view while the first practitioner performs the examination at a remote site. Kit 600 thus allows a practitioner to transport container 606 from one location to another, and to remotely, wireless, transfer video images to monitor 190, thereby achieving wireless video transfer. It will be appreciated that it is also possible to provide power to container 606 through the use of a transformer coupled to jack 618 and an AC power source.

When the practitioner is finished taking video images of a particular object, the practitioner may place each of the components back into the container 606, then readily transport the entire kit 600 to another location, recharging the battery within the container 606 and or the battery within second housing 608 using the cigarette light port as the practitioner travels to the other location.

Another advantage to portable kit 600 is that the practitioner is able to readily adjust the location of monitor 190 such that the practitioner can more readily view the monitor while performing an endoscopic examination, for example.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A portable, hand-held fiber-optic apparatus for producing video images of an object, the portable, hand held apparatus, comprising:

light source means for producing light for illumination of the object, video imaging means for generating a video signal of the object;

lens means having a proximal end and a distal end, said lens means being optically coupled at its proximal end to the video imaging means for translating an image of said object from the distal end of said lens means to the video imaging means, said lens means having optical fibers configured to transmit light from the light source means to the object so as to illuminate the object;

power supply means electrically coupled to, and for supplying electrical power to said light source means and said video imaging means; and a housing configured to house the light source means, the video imaging means, the proximal end of the lens means, and the power supply means within the housing, such that the apparatus is self-contained, wherein the lens means is optically coupled at its proximal end to the light source means; and further comprising a sleeve mounted on the proximal end of the lens means and a portion of the light source means such that the sleeve tightly fits about (i) an exterior surface of the proximal end of the lens means and (ii) an exterior surface of a portion of the light source means such that the light source is in a fixed relationship with respect to the proximal end of the lens means.

2. An apparatus as recited in claim 1, wherein the light source means includes a light bulb having a wattage in the range of about 1 Watt to 5 Watts.

3. An apparatus as recited in claim 1, further comprising a transmitter electrically coupled to the video imaging means and mounted within a housing so as to transmit video signals from within the housing.

4. An apparatus as recited in claim 1, wherein the power supply means supplies less than about 12 volts of electrical power to the light source means.

5. An apparatus as recited in claim 1, wherein said lens means is optically coupled at its proximal end to the light source means for translating light from the light source means to the distal end of the lens means and for emitting the translated light from the distal end of the lens means so as to illuminate the object when the distal end of the lens means is positioned adjacent the object.

6. An apparatus as recited in claim 1, wherein the light source means comprises a flashlight bulb having a wattage of about 1.4 Watts.

7. An apparatus as recited in claim 1, wherein the light source comprises a low wattage light source and includes a light bulb having a wattage in the range of about 0.5 Watts to 5 Watts; and wherein the housing comprises a single housing configured to house the light source, the video imaging, the proximal end of the lens means, and the power supply within the housing, such that the apparatus is self-contained.

8. A portable, hand-held fiber-optic apparatus for producing video images of an object, the portable, hand held apparatus, comprising:

low wattage light source means for producing light for illumination of the object, video imaging means for generating a video signal of the object;

lens means having a proximal end and a distal end, said lens means being optically coupled at its proximal end to the video imaging means for translating an image of said object from the distal end of said lens means to the video imaging means, said lens means having optical fibers configured to transmit light from the light source means to the object so as to illuminate the object;

power supply means electrically coupled to, and for supplying electrical power to said light source means and said video imaging means, wherein the low wattage light source means includes a light bulb having a wattage in the range of about 0.5 Watts to 5 Watts; and a single housing configured to house the light source means, the video imaging means, the proximal end of the lens means, and the power supply means within the housing, such that the apparatus is self-contained;

wherein the distal end of the light source means abuts the proximal end of the lens means.

9. An apparatus as recited in claim 1, wherein a single housing houses the light source means, a proximal portion of the lens means, and the entire video imaging means within an interior cavity of the single housing, the housing having an opening therein, the opening receiving the lens means therein and further comprising a transmitter electrically coupled to the video imaging means, the transmitter configured to transmit video signals generated by the video imaging means, the transmitter being enclosed within the housing such that transmission of video signals occurs in a convenient, cordless manner.

10. An apparatus as recited in claim 1, wherein the apparatus is battery operated.

11. A self-contained, portable, hand-held fiber-optic apparatus for producing video images of an object, the portable, hand held apparatus, comprising:

a light source configured to produce light for illumination of the object;

a video imaging system for generating a video signal of the object;

a lens system having a proximal end and a distal end, said lens system being optically coupled at its proximal end to the video imaging system, the lens system configured to translate an image of said object from the distal end of said lens system to the video imaging system, said lens system having optical fibers configured to transmit light from the light source to the object so as to illuminate the object; and a power supply electrically coupled to, and configured to supply electrical power to said light source and said video imaging system; and a hand-held housing configured to house the light source, the video imaging system, and the proximal end of the lens system, wherein the lens system is optically coupled at its proximal end to the light source and further comprising a sleeve mounted on the proximal end of the lens system and a portion of the light source such that the sleeve fits about (i) an exterior surface of the proximal end of the lens system and (ii) an exterior surface of a portion of the light source such that the light source is in a fixed relationship with respect to the proximal end of the lens system.

12. An apparatus as recited in claim 11, wherein the power supply comprises a battery.

13. An apparatus as recited in claim 11, further comprising:

a housing for housing the power supply.

14. An apparatus as recited in claim 11, further comprising a transmitter, electrically coupled to the video imaging system, for transmitting video signals generated by said video imaging system.

15. An apparatus as recited in claim 11, wherein the housing comprises a single, hand-held housing having an interior surface and an exterior surface, the housing configured to enclose, within the interior thereof, the light source, the entire video imaging system, and the proximal end of the lens system, wherein the housing has an opening therein, the opening being configured to receive the lens means; wherein the apparatus is capable of being held and operated with only a single hand of a user.

* * * * *

UNITED STATES PATENT AND TRADEMARK OFFICE
CERTIFICATE OF CORRECTION

PATENT NO. : 6,692,432 B1
DATED : February 17, 2004
INVENTOR(S) : Yarush et al.

It is certified that error appears in the above-identified patent and that said Letters Patent is hereby corrected as shown below:

Column 5,
Line 46, before "another" delete "a"

Column 7,
Line 38, insert -- , -- after "Jacksonville"
Line 60, insert -- the -- after "required to focus"

Column 10,
Line 45, delete "FIGS. 34" and insert -- FIGS. 3-4 --

Column 13,
Line 47, after "one example of" delete "a"

Column 14,
Line 51, change "on of ports" to -- one of ports --

Column 16,
Line 29, change "sleeve 438" to -- sleeve 430 --

Column 18,
Line 3, insert -- the -- after "hold and operate"
Line 65, change "FIGS." to -- FIG. --

Column 20,
Line 10, insert -- 136 -- after "adjustment notch"

Column 21,
Line 65, change "thumbwheel" to -- thumb wheel --

Column 23,
Line 13, change "thumbwheel" to -- thumb wheel --

Column 24,
Line 21, change "slots 26" to -- slots 26, --

Column 25,
Line 30, after "order" insert -- to --
Line 34, after "opposed to" delete "be"

UNITED STATES PATENT AND TRADEMARK OFFICE
CERTIFICATE OF CORRECTION

PATENT NO. : 6,692,432 B1
DATED : February 17, 2004
INVENTOR(S) : Yarush et al.

It is certified that error appears in the above-identified patent and that said Letters Patent is hereby corrected as shown below:

Column 26,
Line 10, change "though" to -- through --
Line 34, change "mates" to -- mate --

Column 29,
Line 50, insert -- is -- before "preferably disposed"

Column 30,
Line 41, change "air plane" to -- airplane --

Column 31,
Line 10, insert -- , -- after " a practitioner may"
Line 10, insert -- , -- after "container 606"
Line 10, delete "and" before "make a video image"

Column 32,
Line 19, insert -- , -- after "for example"

Column 33,
Line 42, insert -- means -- after the first occurrence of "source"
Line 46, insert -- means -- after "video imaging"
Line 47, insert -- means -- after "power supply"

Column 34,
Line 63, after "lens" delete "means"

Signed and Sealed this

Nineteenth Day of October, 2004

JON W. DUDAS
*Director of the United States Patent and Trademark Office*